US010850033B2

(12) United States Patent
Kovelman

(10) Patent No.: US 10,850,033 B2
(45) Date of Patent: Dec. 1, 2020

(54) PREDICTED TIME TO ASSESS AND/OR CONTROL A GLYCEMIC STATE

(71) Applicant: MEDTRONIC MINIMED, INC., Northridge, CA (US)

(72) Inventor: Paul H. Kovelman, Simi Valley, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 665 days.

(21) Appl. No.: 15/666,342

(22) Filed: Aug. 1, 2017

(65) Prior Publication Data

US 2017/0326296 A1 Nov. 16, 2017

Related U.S. Application Data

(62) Division of application No. 14/103,513, filed on Dec. 11, 2013, now Pat. No. 9,750,877.

(51) Int. Cl.
| | | |
|---|---|---|
| *A61M 5/172* | (2006.01) | |
| *A61B 5/145* | (2006.01) | |
| *A61B 5/00* | (2006.01) | |
| *A61M 5/142* | (2006.01) | |
| *G06F 19/00* | (2018.01) | |

(52) U.S. Cl.
CPC ....... *A61M 5/1723* (2013.01); *A61B 5/14532* (2013.01); *A61B 5/4839* (2013.01); *A61B 5/7275* (2013.01); *A61M 5/14244* (2013.01); *G06F 19/3468* (2013.01);
(Continued)

(58) Field of Classification Search
USPC ...................................................... 600/365
See application file for complete search history.

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

| EP | 2500049 A1 | 9/2012 |
| WO | WO 2008/057384 A2 | 5/2008 |
| WO | WO 2010/135646 A1 | 11/2010 |

OTHER PUBLICATIONS

Greet Van Den Berghe G. et al., Intensive Insulin Therapy in Critically Ill Patients, The New England Journal of Medicine, Nov. 8, 2001, pp. 1359-1367, vol. 345, No. 19.
(Continued)

*Primary Examiner* — Christian Jang
*Assistant Examiner* — Mitchell E Alter
(74) *Attorney, Agent, or Firm* — Lorenz & Kopf, LLP

(57) ABSTRACT

Presented here are techniques for controlling glucose levels of a patient based on predicted time to a target glucose level. One methodology predicts a trajectory of the blood glucose level based on past observations of the blood glucose level, determines a cost expression based on the trajectory, and affects a future command to an infusion pump to affect a cost value according to the cost expression. Another methodology defines a target blood glucose concentration level for the patient, observes a current blood glucose concentration for the patient based on signals received from a blood-glucose sensor, and predicts a duration of time for the patient's blood glucose concentration to reach the target blood glucose concentration level based on the observed current blood glucose concentration.

13 Claims, 14 Drawing Sheets

(52) U.S. Cl.
CPC .. *A61B 5/6849* (2013.01); *A61M 2005/14208* (2013.01); *A61M 2005/1726* (2013.01); *A61M 2230/201* (2013.01)

(56) References Cited

U.S. PATENT DOCUMENTS

| | | | |
|---|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,833,157 B2 | 11/2010 | Gottlieb et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,517,941 B1 | 8/2013 | Wenzel |
| 2007/0123819 A1 | 5/2007 | Mernoe et al. |
| 2007/0128682 A1 | 6/2007 | Rosman et al. |
| 2008/0208113 A1 | 8/2008 | Damian et al. |
| 2009/0054753 A1 | 2/2009 | Robinson et al. |
| 2010/0160861 A1 | 6/2010 | Causey, III et al. |
| 2011/0021898 A1 | 1/2011 | Wei et al. |
| 2011/0313390 A1 | 12/2011 | Roy et al. |
| 2012/0108933 A1 | 5/2012 | Liang et al. |
| 2013/0190583 A1 | 7/2013 | Grosman et al. |

OTHER PUBLICATIONS

Richard N. Bergman, et al., Physiological Evaluation of Factors Controlling Glucose Tolerance in Man, Dec. 1981, pp. 1456-1467, vol. 68, J. Clin. Invest. The American Society for Clinical Investigation, Inc.

Roman Hovorka, et al., Nonlinear Model Predictive Control of Glucose Concentration in Subjects with Type 1 Diabetes, Jul. 22, 2004, pp. 905-920, vol. 25, Institute of Physics Publishing, Physiological Measurement.

Anirban Roy, et al., Dynamic Modeling of Free Fatty Acid, Glucose, and Insulin: An Extended "Minimal Model", 2006, pp. 617-626, vol. 8, No. 6, Diabetes Technology and Therapeutics, Mary Ann Liebert, Inc.

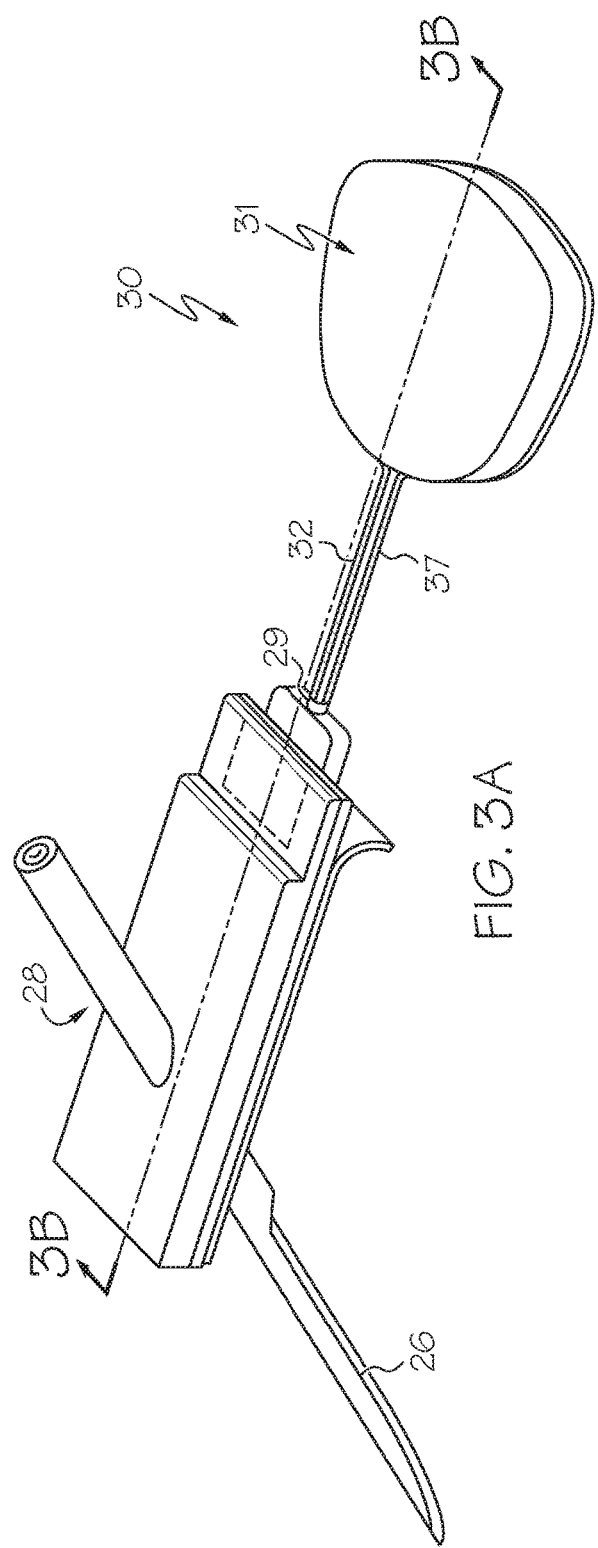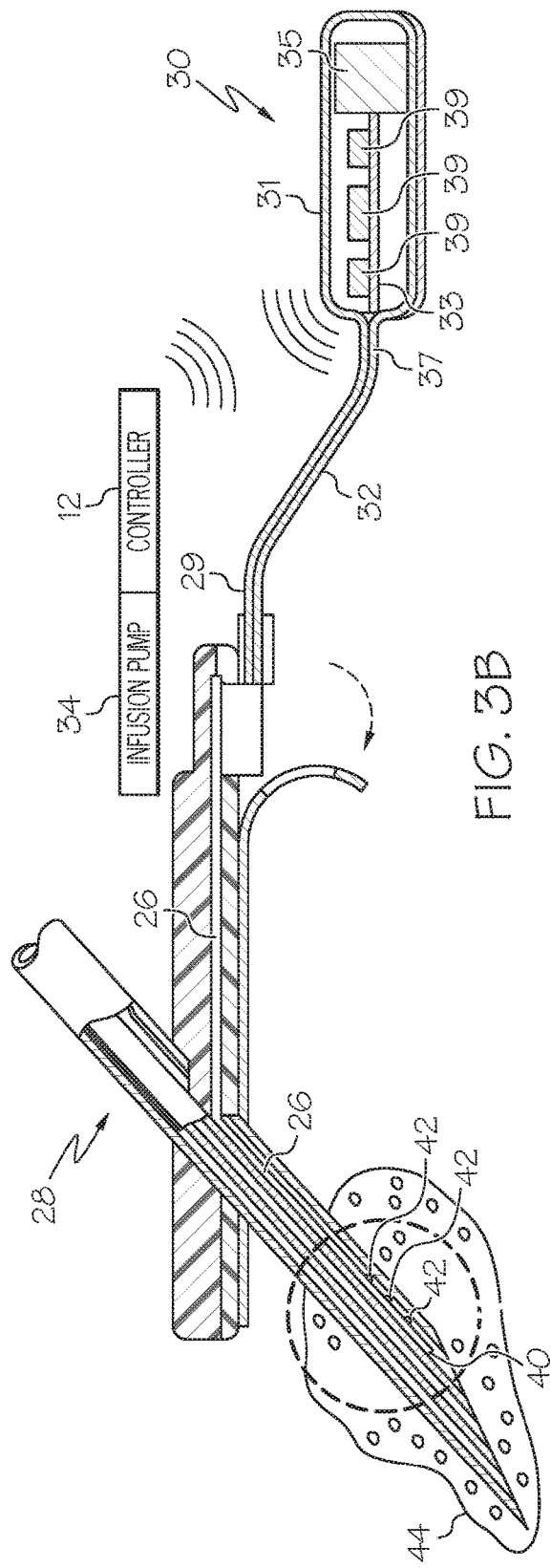

PREDICTED TIME TO ASSESS AND/OR CONTROL A GLYCEMIC STATE

CROSS-REFERENCE TO RELATED APPLICATION

This application is a divisional of U.S. patent application Ser. No. 14/103,513, filed Dec. 11, 2013 and issued as U.S. Pat. No. 9,750,877 on Sep. 5, 2017.

TECHNICAL FIELD

Subject matter disclosed herein relates to monitoring and/or controlling blood glucose levels in patients.

BACKGROUND

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of Type 1 diabetic individuals in the United States were using infusion pump therapy. Presently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

A closed-loop infusion pump system may include an infusion pump that is automatically and/or semi-automatically controlled to infuse insulin into a patient. The infusion of insulin may be controlled to occur at times and in amounts that are based, for example, on blood glucose measurements obtained from an embedded glucose sensor in real-time. Closed-loop infusion pump systems may also employ the delivery of glucose and/or glucagon, in addition to the delivery of insulin, for controlling blood-glucose levels of a patient (e.g., in a hypoglycemic context).

BRIEF SUMMARY

An exemplary embodiment of a method is provided here. The method defines a target blood glucose concentration level for a patient, and observes a current blood glucose concentration for the patient based, at least in part, on signals received from a blood-glucose sensor. The method continues by predicting a duration of time for the patient's blood glucose concentration to reach the target blood glucose concentration level based, at least in part, on the observed current blood glucose concentration.

Also provided is an exemplary embodiment of an apparatus having an insulin infusion pump to deliver insulin to a patient, a glucose sensor to obtain observations of a blood glucose concentration of the patient, and a controller. The controller is used to predict a duration of time for the blood glucose concentration to reach a target level based, at least in part, on a current observation of the blood glucose concentration. The controller generates one or more insulin pump commands to control an operation of the insulin infusion pump based, at least in part, on the predicted duration of time.

An exemplary embodiment of an article is also provided here. The article includes a non-transitory storage medium comprising machine-readable instructions stored thereon which are executable by a special purpose computing device to: define at least one target blood glucose concentration level for a patient; associate at least one threshold time period to each of the at least one target blood glucose concentration level, resulting in a number of time-to-target checkpoints; observe a current blood glucose concentration for the patient based, at least in part, on signals received from a blood-glucose sensor of a glucose control system; predict a respective duration of time for the patient's blood glucose to reach one or more of the at least one target blood glucose concentration level, at least in part, on the observed current blood glucose concentration; checking each predicted duration of time against at least one of the time-to-target checkpoints; and controlling an operation of the glucose control system, based on the checking.

An exemplary embodiment of a method of operating a glucose control system is also presented here. The method predicts a duration of time for a blood glucose concentration of a patient to reach a predefined target level, compares the predicted duration of time to a threshold time period assigned to the predefined target level, and controls a first operation of the glucose control system when the comparing determines that the predicted duration of time is shorter than the threshold time period. The method controls a second operation of the glucose control system when the comparing determines that the predicted duration of time is equal to or longer than the threshold time period.

Another exemplary embodiment of a method is also provided. The method predicts a trajectory of a blood glucose level of a patient based, at least in part, on past observations of the blood glucose level. The method continues by determining a cost expression based, at least in part, on the predicted trajectory, and by affecting at least one future command to at least one infusion pump so as to affect a cost value according to the cost expression.

Another exemplary embodiment of an apparatus is also presented here. The apparatus includes one or more infusion pumps to infuse a substance into a body in response to commands. The apparatus also has a controller that is operated to: predict a trajectory of a blood glucose level of the body based, at least in part, on past observations of the blood glucose level; determine a cost expression based, at least in part, on the predicted trajectory; and affect at least one future command to the one or more infusion pumps so as to affect a cost value according to the cost expression.

Another exemplary embodiment of an article is also provided here. The article includes a non-transitory storage medium comprising machine-readable instructions executable by a special purpose computing apparatus to: predict a trajectory of a blood glucose level of the body based, at least in part, on past observations of the blood glucose level; determine a cost expression based, at least in part, on the predicted trajectory; and affect at least one future command to the one or more infusion pumps so as to affect a cost value according to the cost expression.

An apparatus according to yet another exemplary embodiment is also provided here. The apparatus includes means for predicting a trajectory of a blood glucose level of a patient based, at least in part, on past observations of the blood glucose level. The apparatus also includes means for determining a cost expression based, at least in part, on the predicted trajectory, and means for affecting at least one future command to at least one infusion pump so as to affect a cost value according to the cost expression.

Other alternative embodiments are described herein and/or illustrated in the accompanying Drawings. Additionally, particular embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular embodiments, a sensor may be adapted to generate one or more signals responsive to a measured blood glucose concentration in a body while a special purpose computing device/processor may be adapted to perform at least a portion of described method(s) according to one or more particular implementations based upon one or more signals generated by the sensor.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 3A is a perspective view of a glucose sensor system for use in accordance with an embodiment.

FIG. 3B is a side cross-sectional view of the glucose sensor system of FIG. 3A for an embodiment.

DETAILED DESCRIPTION

Figure 1:
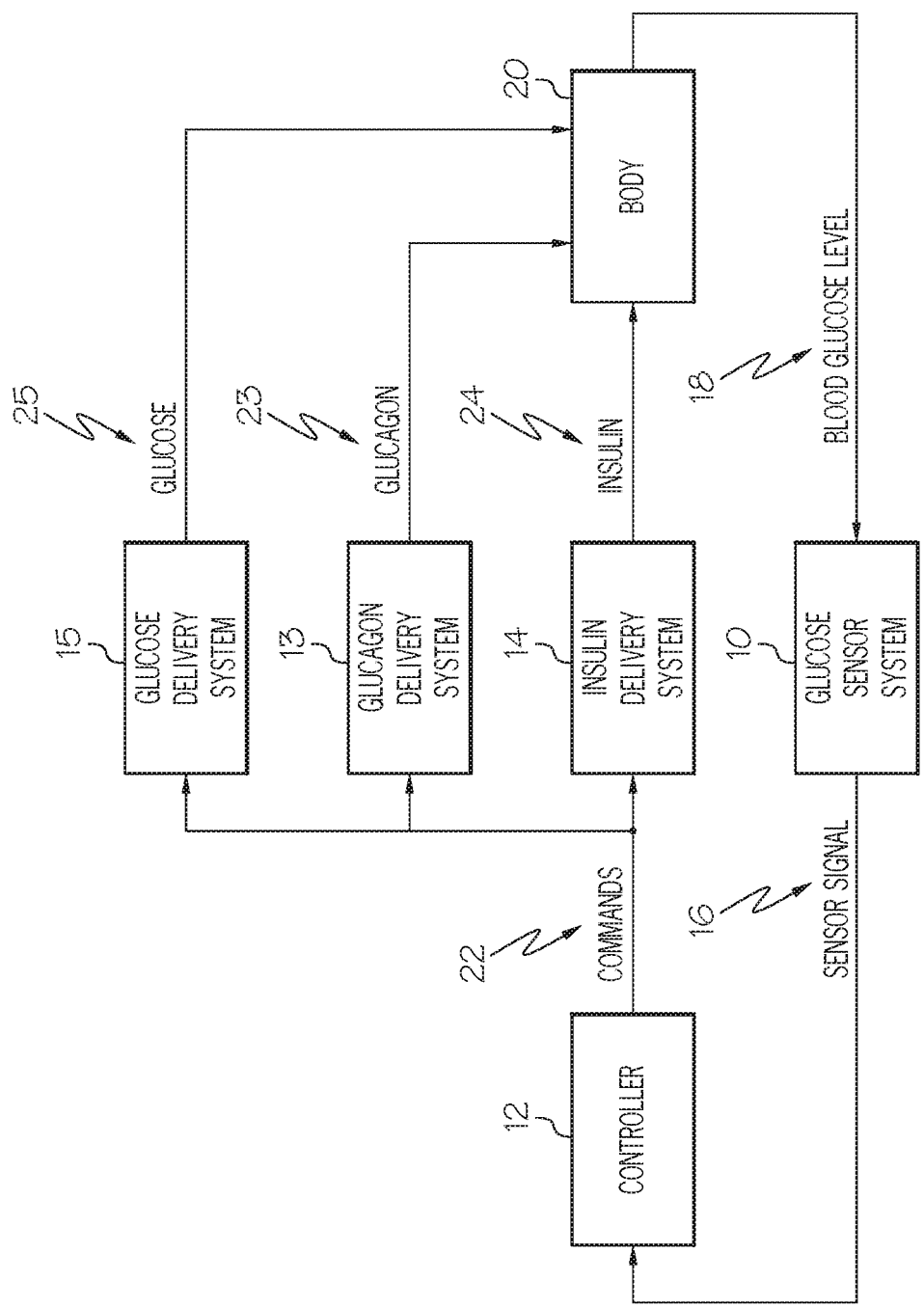
FIG. 1 is a block diagram of a closed loop glucose control system in accordance with an embodiment.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

In an exemplary glucose control system environment, blood-glucose measurements may be employed in a closed loop infusion system for regulating a rate of fluid infusion into a body. In particular embodiments, a control system may be adapted to regulate a rate of insulin, glucagon, and/or glucose infusion into a body of a patient based, at least in part, on a glucose concentration measurement taken from a body (e.g., from a glucose sensor and/or metered blood glucose measurement). In certain implementations, such a system may be designed to model a pancreatic beta cell ($\beta$-cell). Here, such a system may enable a patient to control an infusion device for releasing insulin, glucagon or glucose into the patient's body for effective blood glucose management. Here, such a system may be adapted to control infusion of insulin and/or glucagon so as to control/maintain a patient's blood glucose within a target range, thus reducing the risk that a patient's blood glucose level transitions to dangerous extreme levels in the absence of patient action.

According to certain embodiments, examples of closed-loop systems as described herein may be implemented in a hospital environment to monitor and/or control levels of glucose in a patient. Alternatively, according to certain embodiments, examples of closed-loop systems as described herein may be implemented in non-hospital environments to monitor and/or control levels of glucose in a patient. Here, a patient or other non-medical professional may be responsible for interacting with a closed-loop system.

To maintain healthy glucose levels, a person with type 1 diabetes may manage their glycemia by monitoring blood glucose levels, controlling diet, exercise, and self-administering appropriate amounts of insulin at appropriate times.

Deviations from such glycemic management, such as skipping an insulin bolus at meal time or underestimating the carbohydrate content of a meal may bring about prolonged hyperglycemia. Likewise, receiving too much insulin (e.g., by over-bolusing) for a given blood glucose level and/or meal may bring about severe hypoglycemia. Other external factors, such as exercise or stress, may also contribute to glycemic deviations.

In a particular embodiment of a closed-loop system, such a system may be adapted to control infusion of insulin and/or glucagon so as to control/maintain a patient's blood glucose within a target range, thus reducing the risk that a patient's blood glucose level transition to dangerous extreme levels. Again, such a mechanism may reduce the risk of hypoglycemia and hyperglycemia if a patient, non-medical professional or medical professional is not fully attentive to providing inputs to the system for effective glycemic management.

According to an embodiment, depending on a patient's particular physiology, a target or set-point glucose level may be established. For example, such a target or set-point glucose level may be defined based, at least in part, on guidelines established by the American Diabetes Association (ADA) and/or clinical judgment of a patient's physician. Here, for example, the ADA has recommended a pre-prandial blood glucose concentration of between 80-130 mg/dl, which is in the normal glycemic range. Alternatively, target or set-point glucose level may be fixed at 120 mg/dl. In yet another alternative, a target or set-point blood glucose concentration may vary over time depending on particular patient conditions. It should be understood, however, that these are merely examples of a target or set-point blood glucose concentration, and claimed subject matter is not limited in this respect.

According to an embodiment, a closed-loop system may be employed to maintain a patient's glucose level in a range about a predetermined set-point or target level as described in U.S. patent application Ser. No. 12/820,944, filed on Jun. 22, 2010, and assigned to the assignee of claimed subject matter. Here, insulin may be infused to the patient at a predetermined basal rate while the patient's glucose level is within the predetermined range. If the glucose level escapes that range, a different infusion rate may be applied based, at least in part, on the predetermined set-point or target level. For example, if the patient's glucose level exceeds the range, an insulin infusion rate may be increased. In another example, if the patient's glucose level falls below a particular level, an insulin infusion rate may be reduced from the predetermined basal rate. Of course, these are merely examples of how the insulin infusion rate may be changed if a patient's glucose level escapes a particular range, and claimed subject matter is not limited in this respect.

By maintaining a predetermined basal insulin infusion rate while the glucose level is within a target range, extreme glycemic variations may be reduced or avoided altogether. This may provide a patient with improved glycemic control in circumstances in which they would otherwise be exposed to undesirable extremes of glycemia. Here, while such a patient may remain in control of insulin infusion decisions, particular embodiments may respond automatically in the absence of particular patient action (e.g., forgetting to bolus insulin to cover a meal) to prevent blood glucose from reaching extreme levels.

A controller may employ any one of several control techniques for computing determining commands for a pump in attempt to maintain a patient's observed blood glucose concentration within a target range. For example, a controller may employ a proportional-integral-derivative (PID) control algorithm in conjunction with controlling a patient's blood glucose level within a particular range as described in U.S. patent application Ser. No. 12/820,944, filed on Jun. 22, 2010, and assigned to the assignee of claimed subject matter. Here, such a PID algorithm may, at least in part, predict a level of blood glucose in a patient at some set time in the future and, based on such a prediction, compute commands to be provided to an infusion pump. While such a PID algorithm may provide an effective technique for maintaining a patient's blood glucose within a target range, a PID algorithm may not fully consider health risks of a blood glucose level being outside of a target range from time to time.

Briefly, according to an embodiment, a predicted blood glucose level of a patient based, at least in part, on past blood glucose measurements and control signals to be applied to at least one infusion pump. A cost expression is determined based, at least in part, on the predicted blood glucose level. The control signals to be applied to the at least one infusion pump may then be affected so as to achieve a cost value according to said cost expression. In one particular implementation, that cost expression is determined based, at least in part, on a predicted duration that that the blood glucose is to be outside of a target range over some interval in the future. Accordingly, the control signals applied to the at least on infusion pump may be responsive to risks associated with the patient's blood glucose level being outside of the target range.

As pointed out above, insulin infusion therapy may be controlled, at least in part, by techniques for predicting a patient's blood glucose level or glycemic state at some point or time in the future (e.g., using a PID algorithm as discussed above). In this context, a "glycemic state" may be determined based on one or more factors such as, for example, a blood glucose concentration. Algorithms may receive measurements or observations of a patient's blood glucose concentration from, for example, a continuous blood glucose monitoring device processing signals from a blood-glucose sensor inserted into subcutaneous tissue. However, merely predicting a blood glucose level at some time in the future may have limited utility in applying a therapy to a patient. For example, systems that predict a blood glucose concentration at some time in the future may merely provide a single blood glucose level prediction for a single instance in the future, and may not fully characterize a patient's glycemic state, or transitions from an initial glycemic state to a possible future glycemic state, for the purpose of applying an appropriate therapy.

In another implementation, insulin infusion therapy may be affected or controlled by a prediction of a duration of time until a patient's current glycemic state or blood glucose level is to reach a target blood glucose concentration or glycemic state. Among other factors, this predicted duration may be based, at least in part, on observations of the patient's current blood glucose level according to signals received from a blood-glucose sensor. This predicted duration may then be used for determining how the patient's therapy may be altered by, for example, changing a rate of insulin infusion.

Predicting a duration of time until a patient is to reach a particular blood glucose level starting from an initial state may enable techniques for characterizing a patient's glycemic state that may not be possible with predicting the patient's blood-glucose level in the future alone. Additionally, a predicted time until a patient reaches a particular glycemic state may enable an enhanced ability to for closed-loop insulin infusion systems.

FIG. 1 is a block diagram of an example closed-loop glucose control system in accordance with an embodiment. Particular embodiments may include a glucose sensor system 10, a controller 12, an insulin delivery system 14, a glucagon delivery system 13, and a glucose delivery system 15, as shown in FIG. 1. In certain exemplary embodiments, glucose sensor system 10 may generate a sensor signal 16 representative of blood glucose levels 18 in body 20, and it may provide sensor signal 16 to controller 12. Controller 12 may receive sensor signal 16 and generate commands 22 that are communicated to insulin delivery system 14, glucagon delivery system 13, and/or glucose delivery system 15. Insulin delivery system 14 may receive commands 22 and infuse insulin 24 into body 20 in response to commands 22. Likewise, glucagon delivery system 13 may receive commands 22 and infuse glucagon 23 into body 20 in response to commands 22. Similarly, glucose delivery system 15 may receive commands 22 and provide glucose 25 into body 20 in response to commands 22.

Glucose sensor system 10 may include a glucose sensor, sensor electrical components to provide a power to a sensor and to generate sensor signal 16, a sensor communication system to carry sensor signal 16 to controller 12, and a sensor system housing for electrical components and a sensor communication system. A glucose sensor may measure blood glucose directly from a blood stream, indirectly via interstitial fluid using, e.g., a subcutaneous sensor, some combination thereof, and so forth, just to name a few examples. As used herein, "blood glucose", "measured blood glucose", "blood glucose concentration", "measured blood glucose concentration", and the like may refer to a glucose level, a blood glucose level, a blood glucose concentration, and so forth that has been obtained via any type of glucose sensor. It should be understood, however that using a blood glucose sensor is only one particular technique for obtaining such observations or measurements, and that other techniques, such as measuring blood glucose inform observations of other body fluids (e.g., observations of the presence of glucose in interstitial fluid using a subcutaneous sensor), may be used without deviating from claimed subject matter.

Controller 12 may include electrical components and software to generate commands 22 for insulin delivery system 14, glucagon delivery system 13, and/or glucose delivery system 15 based on sensor signal 16. Controller 12 may also include a controller communication system to receive sensor signal 16 and provide commands 22 to insulin delivery system 14, glucagon delivery system 13, and/or glucose delivery system 15. In particular example implementations, controller 12 may include a user interface and/or operator interface (not shown) comprising a data input device and/or a data output device. Such a data output device may, for example, generate signals to initiate an alarm and/or include a display or printer for showing status of a controller 12 and/or a patient's vital indicators. Such a data input device may comprise dials, buttons, pointing devices, manual switches, alphanumeric keys, a touch-sensitive display, combinations thereof, and/or the like for receiving user and/or operator inputs. Such a data input device may be used for scheduling and/or initiating insulin bolus injections for meals, for example. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 13 may include an infusion device and/or an infusion tube to infuse glucagon 23 into body 20. Likewise, glucose delivery system 15 may include an infusion device and/or an infusion tube to infuse glucose 25 into body 20. In alternative embodiments, insulin 24, glucagon 23, and/or glucose 25 may be infused into body 20 using a shared infusion tube. In other alternative embodiments, insulin 24, glucagon 23, and/or glucose 25 may be infused using an intravenous system for providing fluids to a patient (e.g., in a hospital or other medical environment). It should be understood, however, that certain example embodiments may include an insulin delivery system 14 without a glucagon delivery system 13 and/or without a glucose delivery system 15.

In particular embodiments, an infusion device (not explicitly identified in FIG. 1) may include infusion electrical components to activate an infusion motor according to commands 22, an infusion communication system to receive commands 22 from controller 12, and an infusion device housing (not shown) to hold the infusion device.

In particular embodiments, controller 12 may be housed in an infusion device housing, and an infusion communication system may comprise an electrical trace or a wire that carries commands 22 from controller 12 to an infusion device. In alternative embodiments, controller 12 may be housed in a sensor system housing, and a sensor communication system may comprise an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within a single housing. In further alternative embodiments, a sensor, a controller, and/or infusion communication systems may utilize a cable, a wire, a fiber optic line, RF, IR, or ultrasonic transmitters and receivers, combinations thereof, and/or the like instead of electrical traces, just to name a few examples.

Figure 2:
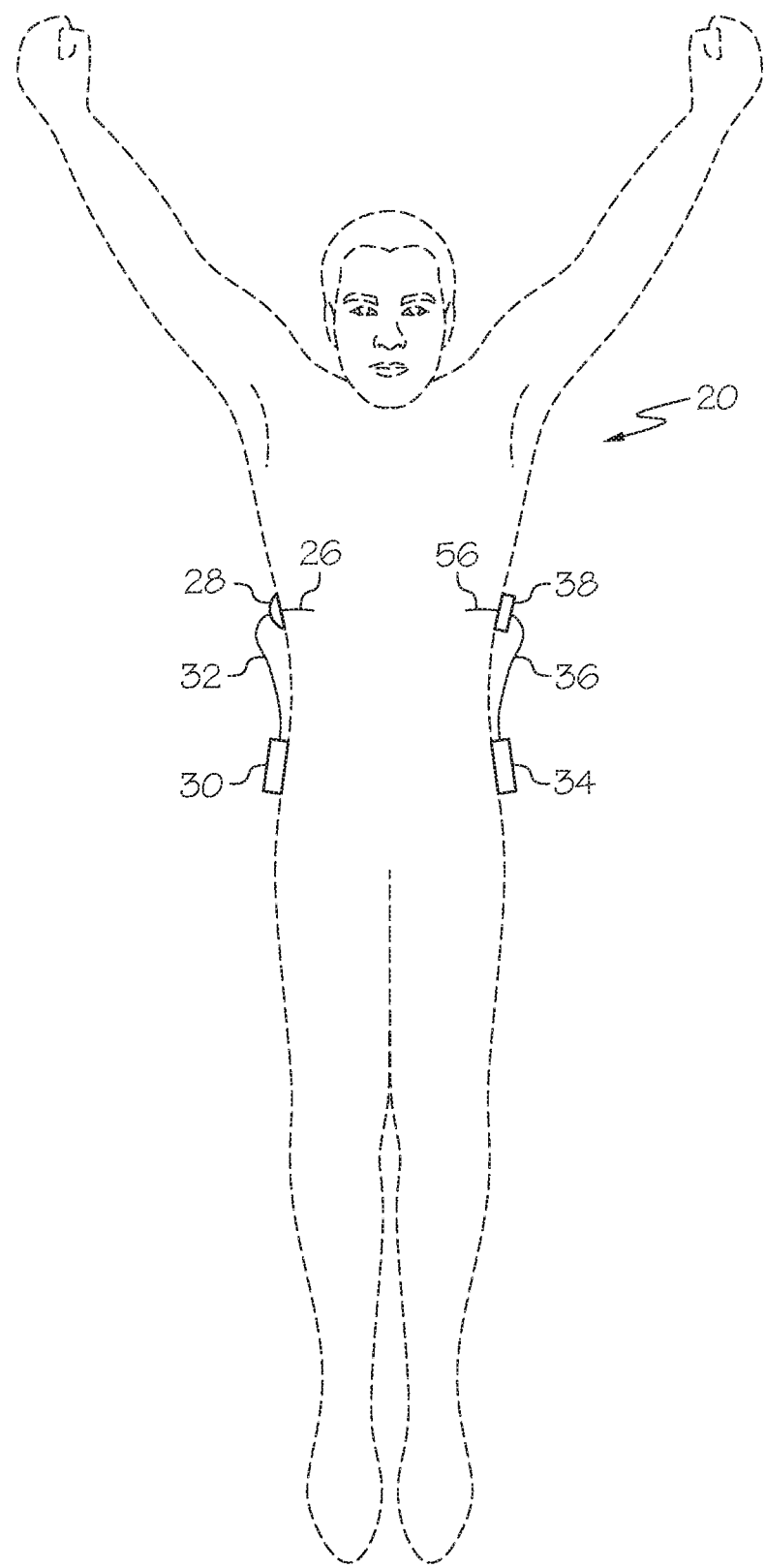
FIG. 2 is a front view of closed loop hardware located on a body in accordance with an embodiment.
Figure 3C:
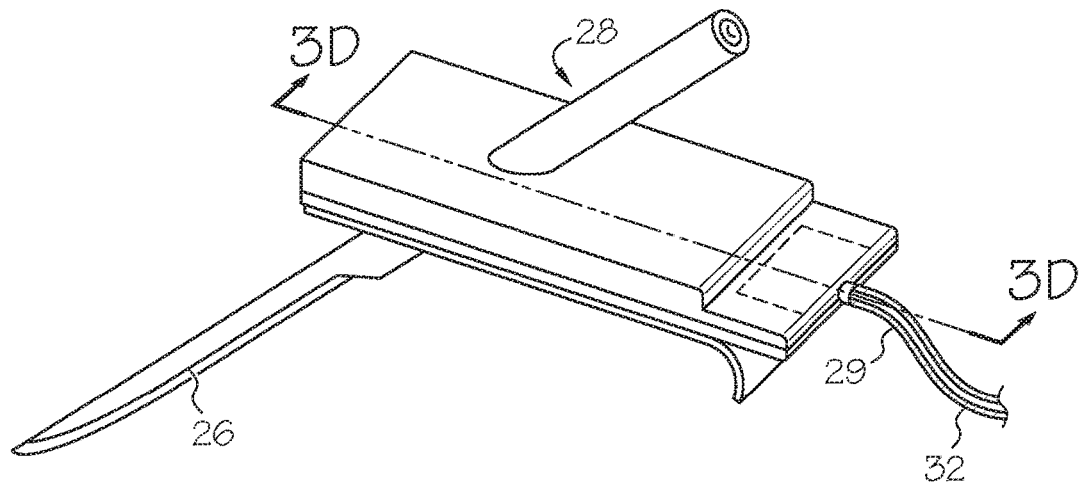
FIG. 3C is a perspective view of a sensor set of a glucose sensor system of FIG. 3A for an embodiment.
Figure 3D:
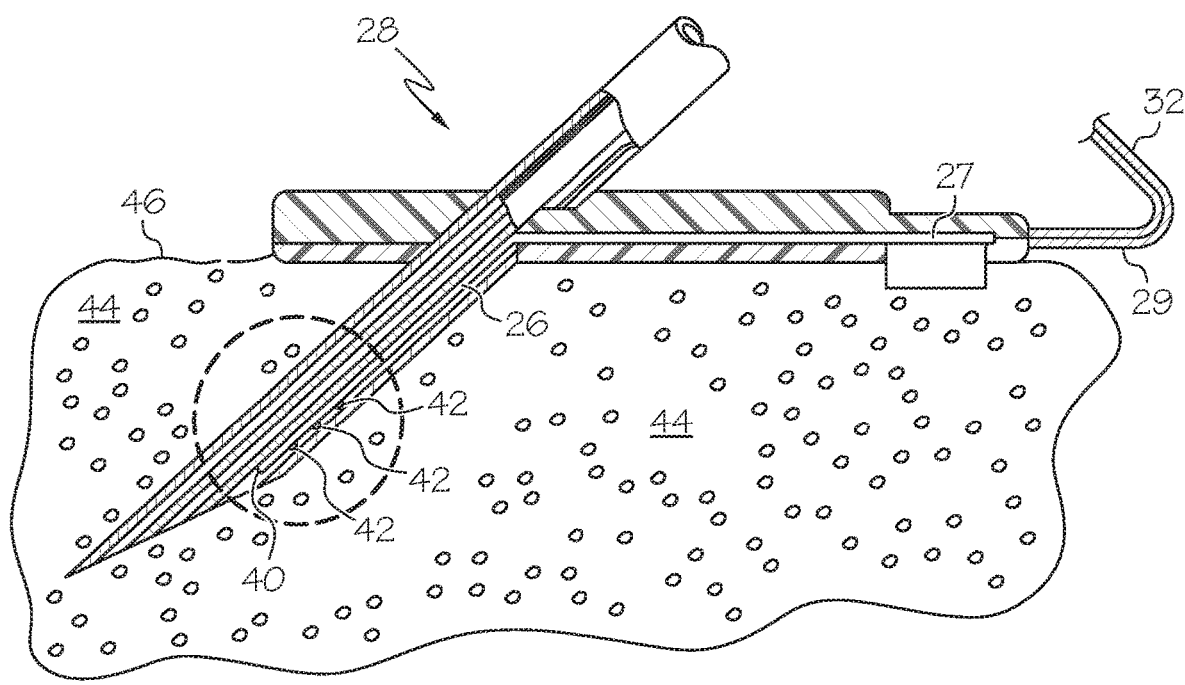
FIG. 3D is a side cross-sectional view of a sensor set of FIG. 3C for an embodiment.
Figure 4:
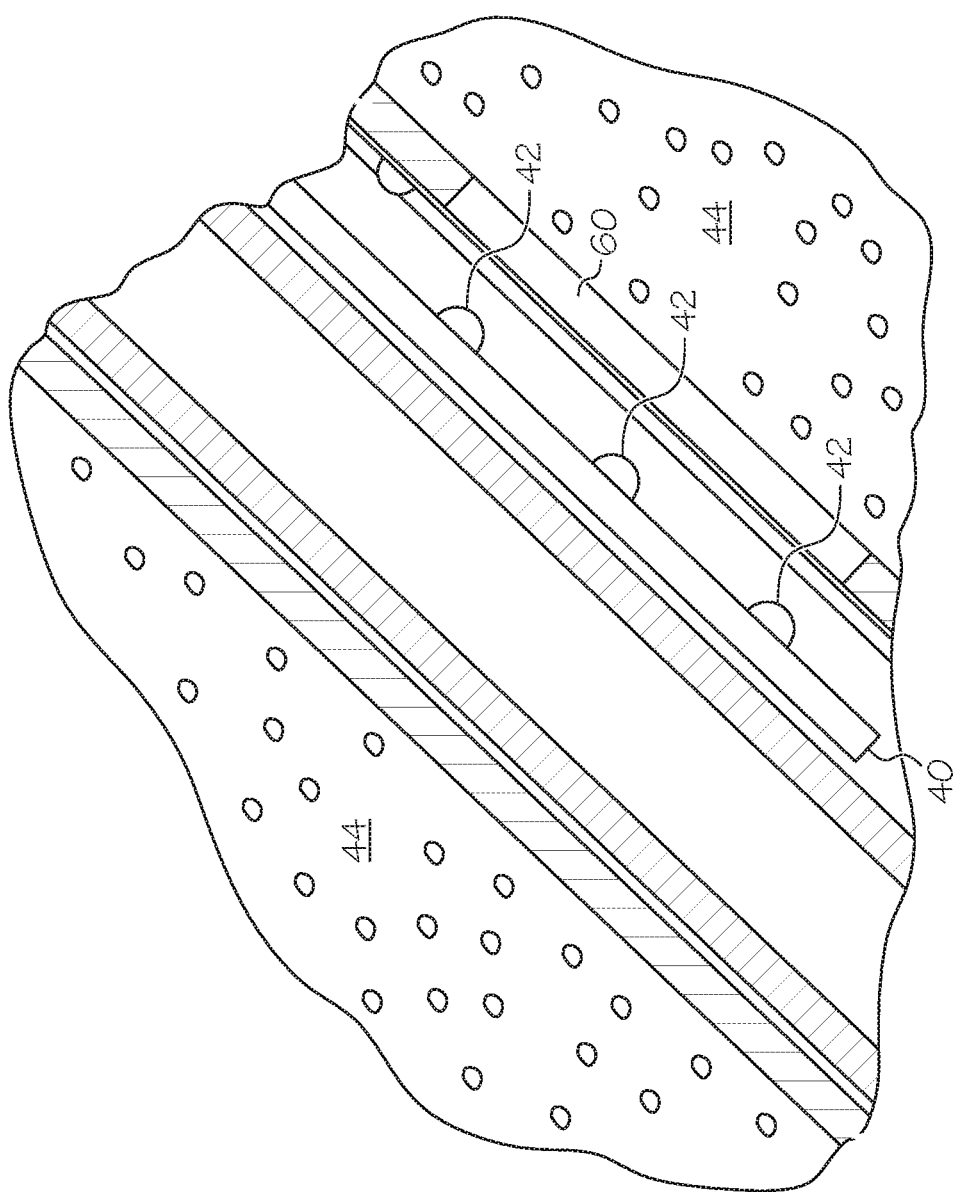
FIG. 4 is a cross sectional view of a sensing end of a sensor set of FIG. 3D for an embodiment.
Figure 5:
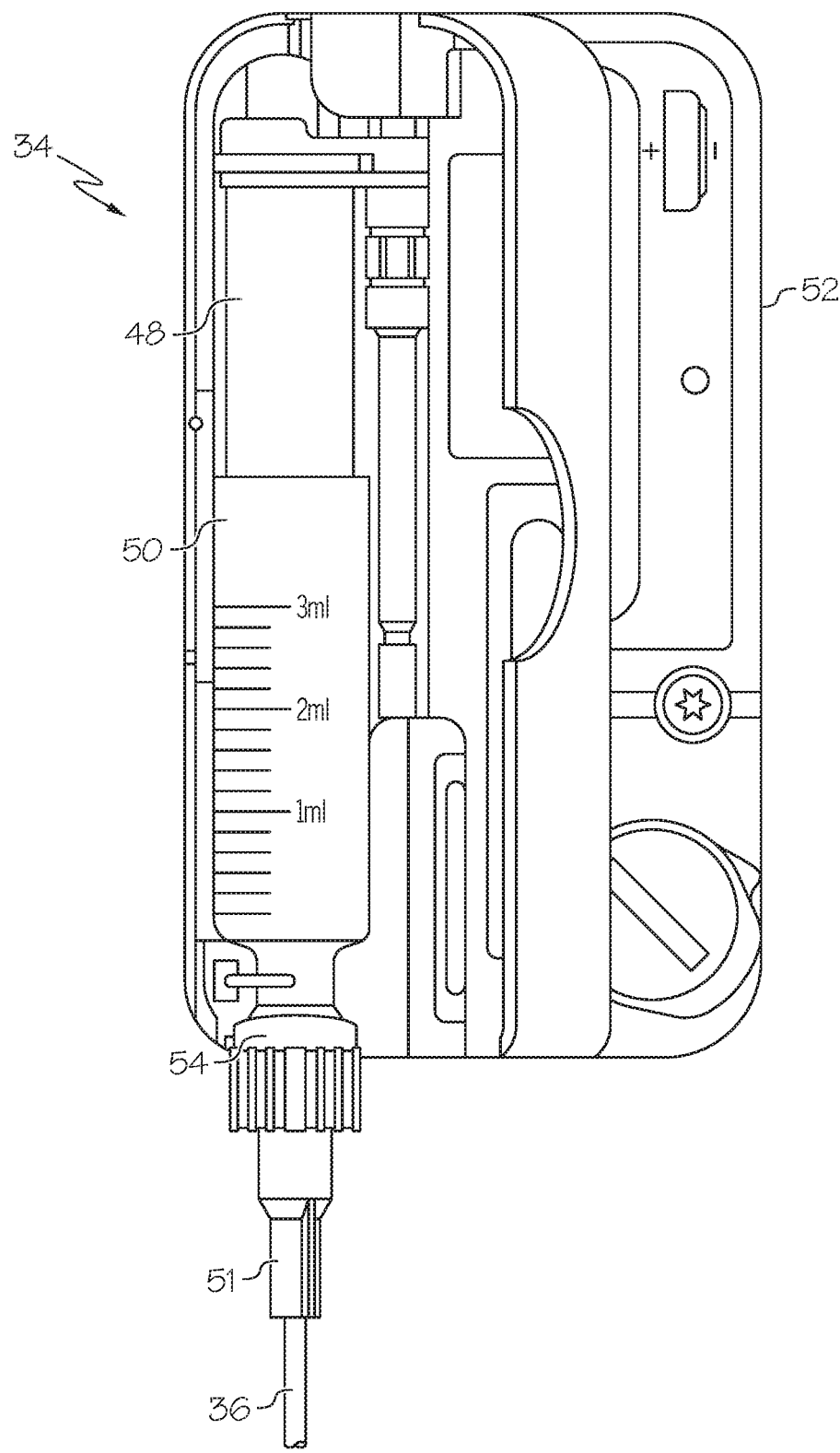
FIG. 5 is a top view of an infusion device with a reservoir door in an open position, for use according to an embodiment.
Figure 6:
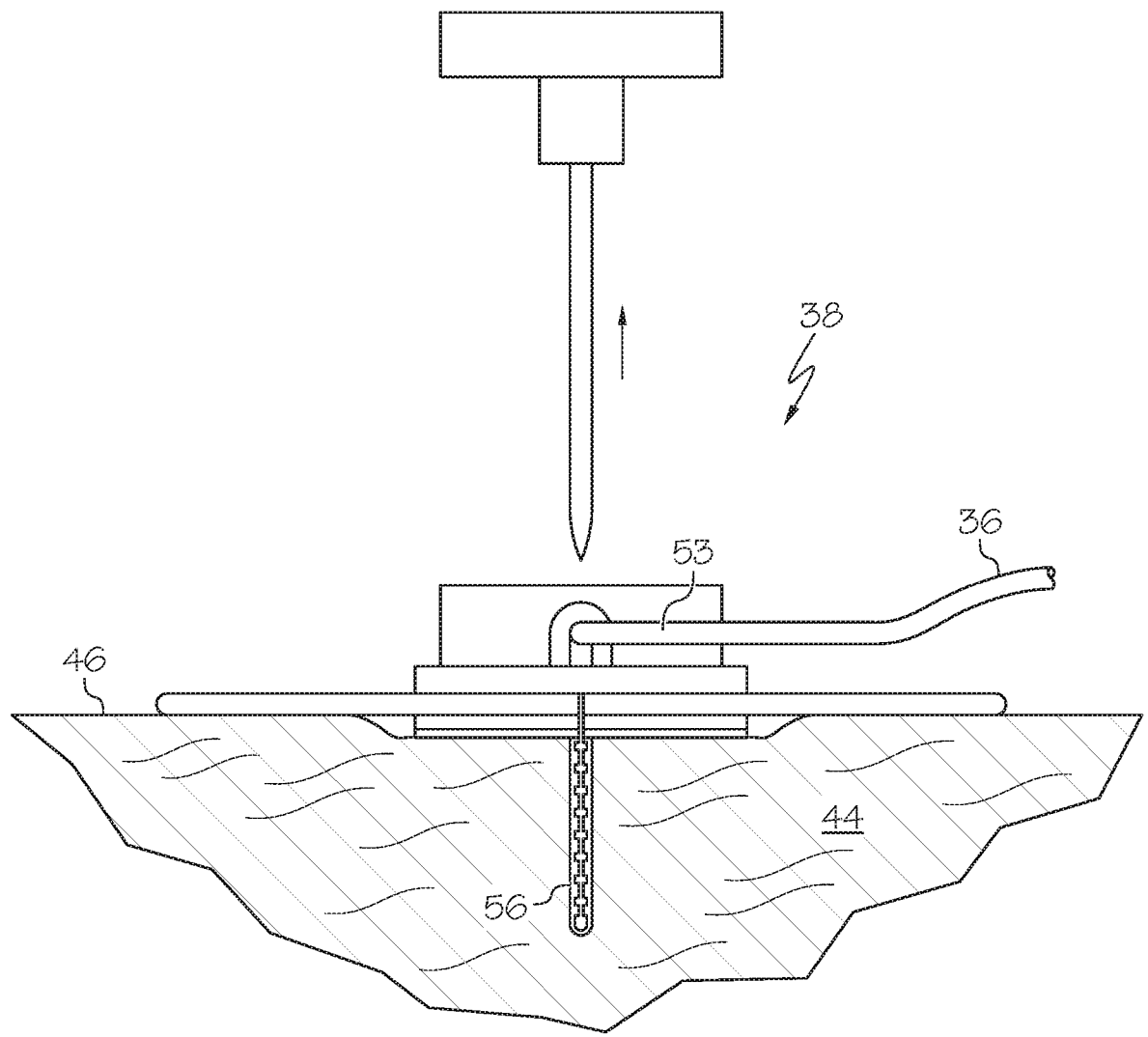
FIG. 6 is a side view of an infusion set with an insertion needle pulled out, for use according to an embodiment.

FIGS. 2-6 illustrate glucose control systems in accordance with certain embodiments. Such glucose control systems may be used, for example, in controlling a patient's glucose level about a target range as discussed above. It should be understood, however, that these are merely examples of particular systems that may be used for controlling a patient's glucose level about a target range and that claimed subject matter is not limited in this respect. FIG. 2 is a front view of closed loop hardware located on a body in accordance with certain embodiments. FIGS. 3A-3D and 4 show different views and portions of an exemplary glucose sensor system for use in accordance with certain embodiments. FIG. 5 is a top view of an infusion device with a reservoir door in an open position in accordance with certain embodiments. FIG. 6 is a side view of an infusion set with an insertion needle pulled out in accordance with certain embodiments.

Particular embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3A and 3B, telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 3D and 4. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 3C and 3D. Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 1, 2, and 5, a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucagon may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 2 and 6). With reference to FIG. 6 (and FIG. 1), insulin 24 (e.g., of FIG. 1) may be forced through infusion tube 36 into infusion set 38 and into body 20 (e.g., of FIG. 1). Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 5) and subcutaneous tissue 44 of a user's body 20.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, glucagon, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 26, sensor set 28, telemetered characteristic monitor 30, sensor cable 32, infusion tube 36, infusion set 38, and so forth. Instead, standard blood glucose meters and/or vascular glucose sensors, such as those described in co-pending U.S. Pat. No. 7,833,157; entitled "MULTILUMEN CATHETER", may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Certain examples of system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that may contribute to a sensor measurement lagging behind an actual present value. Also, as noted herein, such a delay may arise from, for instance, a particular level of noise filtering that is applied to a sensor signal. Such delays and/or time lags in obtaining sensor glucose measurements may ultimately affect closed-loop operation. Accordingly, and as discussed in greater detail below, feedback control mechanisms using various approaches by application of a predicted duration of a blood glucose level being outside of a target range to better address a patient's glycemic health.

Figure 7:
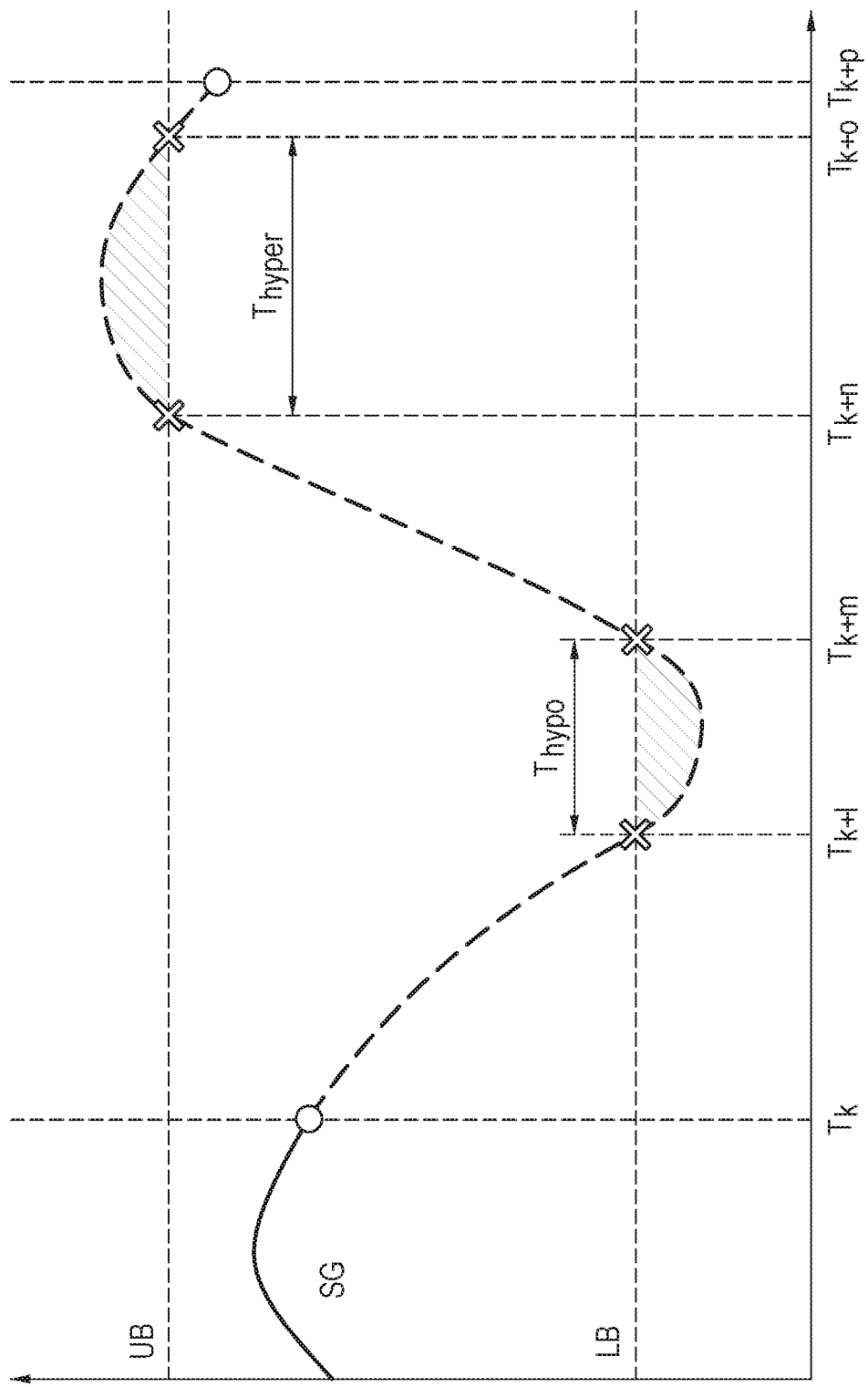
FIG. 7 is a plot of a trajectory of a blood glucose concentration including an observed portion and a predicted portion according to an embodiment.

FIG. 7 is a plot SG of a trajectory of a patient's blood glucose level including a portion up to time $T_k$ that is observed from measurements obtained by a blood glucose sensor indicated by a solid curve portion, and a predicted portion from time $T_k$ until time $T_{k+p}$ as indicated by a broken curve portion. The observed portion of plot SG may be determined from application of filtering techniques to blood glucose sensor measurements known to those of ordinary skill in the art and as shown in U.S. patent application Ser. No. 13/239,265, filed on Sep. 21, 2011, and assigned to the assignee of claimed subject matter. The predicted portion of plot SG may be determined using any one of several techniques such as, for example, that described in: *Physiological Evaluation of Factors Controlling Glucose Tolerance in Man*, R. N. Bergman, L. S. Philips, and C. Cobelli, 1981, J. Clin. Invest., Vol. 68, pp. 1456-1467; *Nonlinear Model Predictive Control of Glucose Concentration in Subjects with Type* 1 *Diabetes*, R. Hovorka, V. Canonico, V. Chassin, et. al. 2004, Physiol. Meas. Vol. 25., pp. 905-920; and *Dynamic Modeling of Free Fatty Acid, Glucose, and Insulin: An Extended "Minimal Model"*, A. Roy and R. S. Parker, Diabetes Technology and Therapeutics, Vol. 8, No. 6, 2006. Of course these are merely examples of techniques that may be used for predicting a patient's blood glucose trajectory and claimed subject matter is not limited in this respect.

As illustrated above with reference with FIG. 1, controller 12 may provide commands 22 to an infusion pump to initiate infusion of glucagon or insulin on periodic command cycles. In addition to sensor measurements used for determining the observed portion of plot SG, techniques for computing the predicted portion of plot SG may also consider past commands 22 generated by a controller and scheduled commands to be provided to one or more infusion pumps.

FIG. 7 further identifies a target range for a patient's blood glucose concentration bounded by a lower bound LB and an upper bound UB. In one particular implementation, a region above upper bound UB may be a hyperglycemic region in which the patient may experience an unwanted hyperglycemic condition. Similarly, a region below lower bound may be a hypoglycemic region in which the patient may experience an unwanted hypoglycemic condition. As shown in FIG. 7, from time $T_{k+l}$ to $T_{k+m}$ (over duration $T_{hypo}$) the predicted portion of plot SG is below lower bound LB, suggesting a risk of hypoglycemia over this duration. Likewise, from time $T_{k+n}$ to $T_{k+o}$ (over duration $T_{hyper}$) the predicted portion of plot SG is above upper bound UB, suggesting a risk of hyperglycemia over this duration.

As pointed out above, a controller may provide commands to one or more infusion pumps on periodic command cycles such as, for example, five minute command intervals. According to an embodiment, commands to one or more infusions pumps (e.g., on command cycles) may be selected or determined so as to affect or minimize a cost expression such as a cost expression as follows:

$$\min_{\Delta U_k} \|\gamma_{hypo} \times T_{hypo}\|_2^2 + \|\gamma_{hyper} \times T_{hyper}\|_2^2 + \|\gamma_U \times \Delta U_k\|_2^2 \quad (1)$$

Where:

$\Delta U_k$ represents a change in an infusion rate from application of particular commands of command set k to one or more infusion pumps;

$\gamma_{hypo}$ is a weight applied for a duration that a blood glucose level is predicted to be in a hypoglycemic region;

$\gamma_{hyper}$ is a weight applied for a duration that a blood glucose level is predicted to be in a hyperglycemic region; and $\gamma_U$ is a weight to be applied for control movement or changes in command settings.

In a particular implementation, a relatively higher value of $\gamma_U$ may tend to make the controller less responsive while a relatively lower value of $\gamma_U$ may tend to make the controller more responsive to changes.

As pointed out above, values for durations $T_{hypo}$ and $T_{hyper}$ are determined by a predicted trajectory of a patient's blood glucose over an interval of interest. The predicted trajectory may be computed based, at least in part, on commands to one or more infusion pumps affecting $\Delta U$. Here, these commands to one or more infusion pumps may be computed and/or selected so as to minimize the cost expression of expression (1).

While the cost expression of expression (1) is affected by a duration that a blood glucose concentration trajectory is predicted to be outside of target range, the cost expression of expression (1) is not affected by or responsive to a degree, magnitude or extent to which the trajectory is predicted to extend outside of the target range. In an alternative implementation, the following expression (2) provides a cost expression that is affected by or responsive to a degree or magnitude to which a predicted trajectory extends outside of a patient's target range for blood glucose:

$$\min_{\Delta U_k} \|\gamma_{hypo} \times AUC_{hypo}\|_2^2 + \|\gamma_{hyper} \times AUC_{hyper}\|_2^2 + \|\gamma_U \times \Delta U_k\|_2^2 \quad (2)$$

Where:

$$AUC_{hypo} = \int_{T_{k+1}}^{T_{k+m}} |PSG(t) - LB| dt$$

-continued $$AUC_{hyper} = \int_{T_{k+n}}^{T_{k+o}} |PSG(t) - UB| dt$$

and PSG(t) is a predicted trajectory of a patient's blood concentration (e.g., the predicted portion of plot SG shown in FIG. 7).

In expression (2), a weight $\gamma_{hyper}$ is applied to a computed "area" bounded by a portion the predicted blood glucose trajectory and extending above the patient's blood glucose target range while a weight $\gamma_{hypo}$ is applied to an area bounded by a portion of the predicted blood glucose trajectory extending below the patient's blood glucose target range. Accordingly, the cost expression of expression (2) is affected by or responsive to a degree or magnitude to which a predicted blood glucose trajectory extends outside of the target range. While cost expressions (1) and (2) provide example cost expressions that account for a predicted duration that a blood glucose trajectory will be outside of a patient's blood glucose level, other cost expressions may be used without deviating from claimed subject matter.

According to an embodiment, a cost expression such as cost expression (1) or (2) may be computed for a set time horizon (e.g., two or three hours) as indicated, for example, by time $T_k$ to $T_{k+p}$ as illustrated in FIG. 7. Also, such a cost expression may be evaluated on command cycles in the process of determining periodic commands to one or more infusion pumps as discussed above. Accordingly, in a particular embodiment, on command cycles, a controller may evaluate possible sets of commands to be applied to one or more infusion pumps and select the possible set that provides the minimum value for the applicable cost expression.

In another embodiment, as pointed out above, a patient's insulin therapy may be altered based, at least in part, on a prediction of a duration of time until the patient's blood-glucose level transitions to a particular target blood-glucose level or glycemic state. As pointed out above, predicting a duration of time until the patient's blood-glucose level reaches a particular target blood-glucose level may enable improved characterization of the patient's glycemic state and transitions between glycemic states, and enable more effective application of insulin infusion or glucose therapies.

It should be understood to those of ordinary skill in the art that a duration of time until a patient at a current blood glucose level reaches a particular target blood-glucose level may be affected by multiple factors. Expression (3) below models a rate of change in a patient's blood glucose level.

$$\frac{d\overline{G}(t)}{dt} = -\frac{1}{\tau_G}\overline{G}(t) - ISFR \cdot \overline{UI}(t) \quad (3)$$

Where:

$\tau_G$ represents a time constant of glucose disappearance;

ISFR represents an insulin sensitivity factor rate (mg/dL/min per U/h);

$\overline{G}(t)$ represents a glucose concentration (mg/dL) at time t; and $\overline{UI}(t)$ represents an insulin infusion rate in deviation variables at time t.

In a particular implementation, values for $\overline{G}(t)$ and $\overline{UI}(t)$ may be calculated as follows:

$$\overline{G}(t) = G(t) - G_{SS}$$

$$\overline{UI}(t) = UI(t) - UI_{SS}$$

Where:
G(t) represents a current blood glucose level;
$G_{SS}$ represents a steady state blood glucose level;
UI(t) represents a current insulin infusion rate; and
$UI_{SS}$ is infusion rate at steady state.

The patient specific parameters, $\tau_G$ and ISFR, can be easily estimated from the historical data (e.g., using observations of a patient's blood concentration collected from a continuous glucose monitoring device and a history of commands provided to an insulin pump). Taking the Laplace transform of expression (3) provides the following expression (4):

$$\overline{G}(s) = \frac{-ISFR \cdot \overline{UI}(s)}{(s + 1/\tau_G)} \quad (4)$$

In particular implementations of insulin therapy, an insulin infusion pump may be controlled in a closed loop system including a continuous glucose monitoring device (e.g., controller 12) as discussed above. An insulin pump may receive command signals at discrete intervals based, at least in part, on real-time observations of a patient's blood glucose level. Here, $\overline{UI}(s)$ may represent a response to a command provided to an insulin infusion pump provided as a step response such that expression (4) may be simplified as expression (5) as follows:

$$\overline{G}(s) = \frac{-\tau_G \cdot ISFR \cdot \overline{U}}{s(\tau_G \cdot s + 1)} \quad (5)$$

Here, $\overline{U}$ represents a magnitude of change in an infusion rate (current minus steady state) in U/h. Taking inverse Laplace transform of expression (5) provides the following:

$$\overline{G}(t) = \tau_G \cdot ISFR \cdot \overline{U}(1 - e^{-t/\tau_G})$$

Rearranging for t provides expression (6) as follows:

$$t = -\tau_G \cdot \ln\left(1 + \frac{\overline{G}}{\tau_G \cdot ISFR \cdot \overline{U}}\right) \quad (6)$$

Here, expression (6) may be applied as a predictor for a duration of time (e.g., a value for t) until a patient's blood glucose level is to approach a particular glucose level or glycemic state based, at least in part, on a current glucose level G(t). In addition to a current glucose level G(t) and a target glucose level $G_{SS}(t)$, expression (6) also considers ISFR and $\tau_G$.

Expression (7) below provides an expression for a predicted duration of time until a patient possibly reaches a particular glycemic state as follows:

$$t_p(G_0, G_f) = -\tau_G \cdot \ln\left(1 + \frac{G_0 - G_f}{\tau_G \cdot ISFR \cdot \Delta U}\right) \quad (7)$$

Where:
$t_p(G_0, G_f)$ is a predicted duration of time for the glycemic state of a subject to transition from a current glycemic state of a blood glucose concentration of $G_0$ to a possible future glycemic state of a blood glucose concentration of $G_f$; and $\Delta U$ represents a magnitude of change in an infusion rate (current minus steady state) in U/h.

It should be understood, however, that expression (7) illustrates merely one technique for predicting a duration of time until a patient's blood glucose concentration reaches a particular glycemic state, and that claimed subject matter is not limited in this respect. Indeed, other expressions or techniques for predicting a time until a patient's blood glucose level is to reach a particular target glycemic state, evaluating the same or different factors, may be used without deviating from claimed subject matter. Additionally, expression (7) provides a predicted time to reach a possible glycemic state under a condition of a steady state insulin infusion rate. It should be understood that other techniques for predicting a duration of time until a blood glucose is reached under conditions of a non-steady state insulin infusion rate may be used without deviating from claimed subject matter. Also, while expression (7) considers a change in an insulin infusion rate, other techniques for predicting a duration of time until a possible glycemic state may be reached may also consider infusions of glucagon (if available).

To illustrate a particular example of predicting a glycemic state according to expression (7), a hypothetical subject may have $\tau_G$=260 min and ISFR=0.3 mg/dL/min per U/h. A current blood glucose concentration at a steady state insulin infusion rate may be at 300 mg/dL. Therefore, time to reach a possible future blood glucose concentration $G_f$ of 70 mg/dL for a step change $\Delta U$ of 3.5 U/h in infusion rate may be predicted according to relation (7) as follows:

$$t_p(300, 70) = -260 \cdot \ln\left(1 + \frac{70 - 300}{260 \cdot 0.3 \cdot 3.5}\right) \approx 481 \text{ min} \quad (8)$$

According to expression (7), a duration of time to reach glucose level of less than 70 mg/dL with the current glucose concentration at 300 mg/dL is 481 min, if the insulin infusion rate is increased by 3.5 U/h from its current state (for that particular patient). As can be observed, expression (7) may be used to affect or select commands to an insulin infusion pump based, at least in part, on an appropriate or desired duration of time to reach a particular glycemic state of $G_f$. If a patient's current glycemic state $G_0$ is in a hyperglycemic region, for example, commands to an insulin infusion pump may increase $\Delta U$ to shorten a duration of time for the patient to reach a more desirable glycemic state of $G_f$. Similarly, commands to an infusion pump may decrease $\Delta U$ to lengthen a duration of time for the patient to reach a more desirable glycemic state of $G_f$. It should be understood, however, that these are merely examples of how expression (7) may be applied in determining or tailoring insulin infusion pump commands to affect a predicted duration of time for a patient to reach a possible future glycemic state, and claimed subject matter is not limited in this respect.

Figure 8:
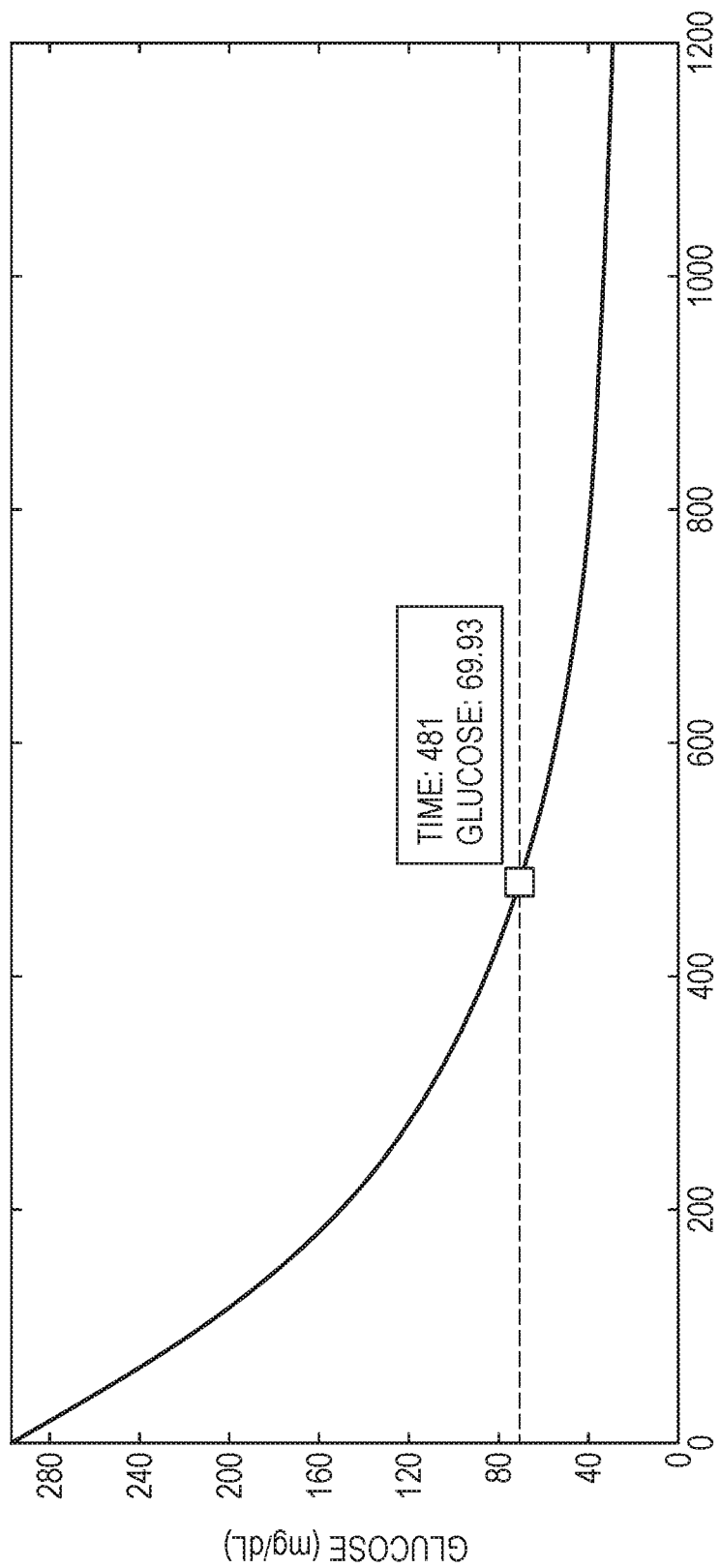
FIG. 8 is a plot of an exemplary predicted duration of time until a particular glycemic state is reached according to an embodiment.

FIG. 8 shows a plot of a duration of time to reach a glycemic state from an initial glycemic state of a current blood glucose concentration of 300 mg/dL (starting at time=0) and a steady state insulin infusion rate. Here, the plot of FIG. 8 may characterize a duration of time to transition to a complete range of possible future glycemic states given values for $\tau_G$=260 min and ISFR=0.3 mg/dL/min per U/h. Accordingly, in addition to merely determining a predicted duration of time to reach a particular target blood glucose concentration, the plot of FIG. 8 may be used to characterize durations of time to reach multiple different blood glucose concentration levels between the current blood glucose concentration (at t=0) to the target blood glucose concentration. As pointed out above, a trend illustrated by the plot of FIG. 8 may better characterize how a patient may transition between particular glycemic states than is available with systems that merely predict a glycemic state at a set point of time in the future.

Similarly, expression (7) may be modified to provide multiple durations of time to reach a plurality of different glycemic states between $G_0$ to $G_f$ as $t_p(G_0, G_1, G_2, \ldots, G_f)$ to generate a prediction of durations of time to reach glycemic states of $G_1, G_2, \ldots, G_f$. Here, a vector of possible future glycemic states $G_1, G_2, \ldots, G_f$ may be provided as input values to $t_p(G_0, G_1, G_2, \ldots, G_f)$ to provide a corresponding output values $t_{p1}, t_{p2}, \ldots, t_{pf}$ predicting durations of time. In a case of $G_0 > G_f$, other glycemic states may be set as $G_0 > G_1 > G_2 > \ldots > G_f$. Here, if $G_0$ is in a hyperglycemic range, for example, values of $G_1$ and $G_f$ may define upper and lower bounds of a target blood glucose control range about an ideal target glycemic state of $G_2$. As may be observed, for a condition of given values of $\Delta U$, $\tau_G$, ISFR, and $G_0$ in expression (7), not all values of $G_f$ may be feasibly reached. If a patient's current glycemic state $G_0$ is in a hypoglycemic region, for example, application of insulin according to $\Delta U$, without any addition of glucose to the patient's blood plasma (e.g., from infusion of glucagon or a meal), may not raise the patient's blood glucose to a higher, target value. Indeed, by inspection, expression (7) has an infeasible or undefined value for $t_p(G_0, G_f)$ under the following condition:

$$\frac{G_f - G_0}{\tau_G \cdot ISFR \cdot \Delta U} > 1.0$$

In a particular implementation of controller 12 discussed above, a predicted duration of time until a patient's glycemic state reaches a particular blood glucose may be computed based, at least in part, on observations of a patient's blood glucose level obtained from monitor glucose sensor system 10 and commands provided to insulin delivery system 14.

As mentioned above with reference to the plot shown in FIG. 8, a glucose control system according to the embodiments described here can be designed to predict the patient's future blood glucose concentration level based on a currently observed sensor glucose reading, historical sensor data, historical insulin pump data, etc. Moreover, the glucose control system can be suitably configured to predict a period of time (relative to the current time) that it will take for the patient to reach a specified and predetermined target blood glucose concentration level. The specified target level has at least one threshold time period associated therewith, and the predicted time period is compared to the threshold time period(s) as needed. The glucose control system may take any appropriate type of action that considers the results of the comparison.

The glucose control system may be configured to define and consider any number of different target blood glucose concentration levels (also referred to here simply as "target levels" for the sake of brevity) for the patient, including only one target level if so desired. Moreover, the glucose control system may be configured to define and assign one or more different threshold time periods to each target level. Furthermore, the glucose control system may be configured to define and associate any number of different operations, actions, features, or functions to the various combinations of target levels and threshold time periods. As used here, "time-to-target checkpoint" refers to a target blood glucose level and an associated threshold time period. In this regard, a time-to-target checkpoint represents a decision point that can potentially lead to a change in the current operating state of the glucose control system. Accordingly, a time-to-target checkpoint may have one or more system operations associated therewith.

Figure 9:
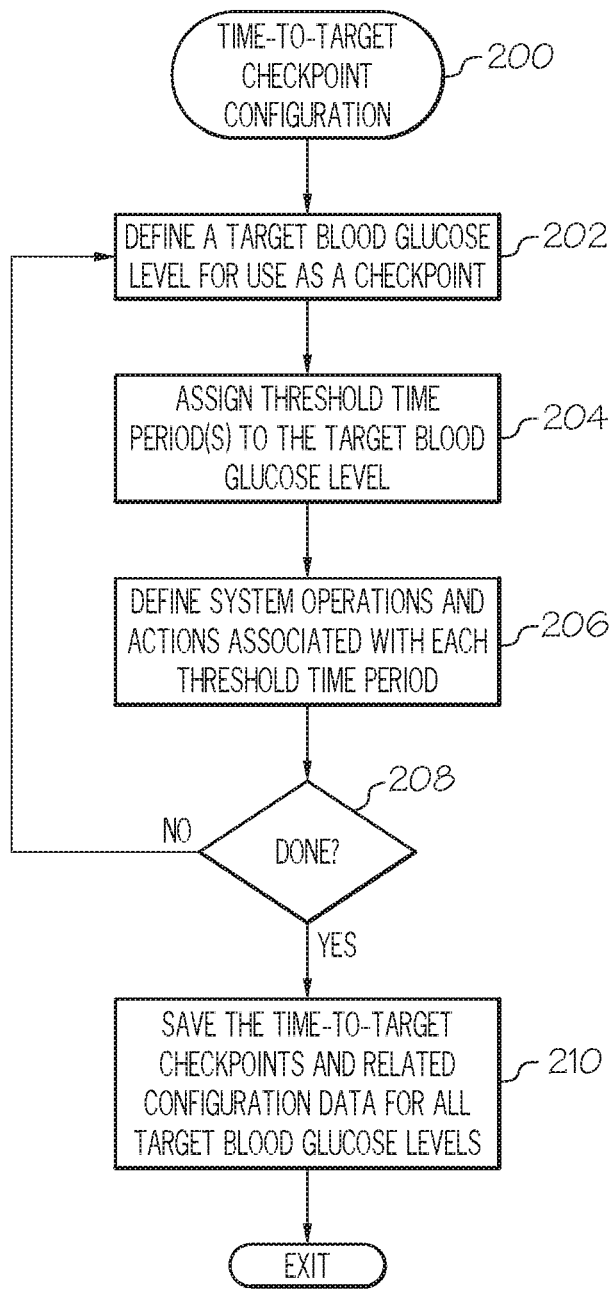
FIG. 9 is a flow chart that illustrates an exemplary embodiment of a process that may be performed to configure certain time-to-target checkpoints in a glucose control system.

FIG. 9 is a flow chart that illustrates an exemplary embodiment of a configuration process 200 that may be performed to configure certain time-to-target checkpoints in a glucose control system. The various tasks performed in connection with a process described here may be performed by software, hardware, firmware, or any combination thereof. An illustrated process may be described here with reference to elements mentioned above in connection with FIGS. 1-8. It should be appreciated that a described process may include any number of additional or alternative tasks, the tasks shown in a given figure need not be performed in the illustrated order, and a described process may be incorporated into a more comprehensive procedure or process having additional functionality not described in detail herein. Moreover, one or more of the tasks shown in the figures could be omitted from an embodiment of the illustrated process as long as the intended overall functionality remains intact.

The process 200 may be performed as a preliminary routine at any time to prepare the host glucose control system to carry out the techniques and methodologies described in more detail below. In practice, the process 200 could be performed by the patient, a caregiver, or anyone having access to the configuration settings of the glucose control system. To this end, the process 200 may be responsive to user input received at one or more user interface elements of the glucose control system itself (e.g., a touch screen). Alternatively or additionally, the process 200 may be responsive to remotely entered commands or control signals that are received, processed, and executed at the glucose control system.

The process 200 defines a first target blood glucose concentration level for the patient (task 202). The defined target level will ultimately be used for at least one time-to-target checkpoint, as explained in more detail below. Depending on the implementation, the system may provide a predefined list of selectable target levels, or it may enable the user to enter any supported target level (typically expressed in units of mg/dl). In this regard, the system may place practical upper and lower limits such that only valid target levels can be designated. For example, the process 200 may be designed such that the defined target level must be within the range of 30 to 300 mg/dl. In alternative embodiments, different ranges could be used, such as: 50 to 200 mg/dl; 60 to 180 mg/dl; 70 to 150 mg/dl; 80 to 120 mg/dl; or the like. These different ranges are merely presented as some possible examples. The disclosed embodiments may utilize any desired target range, and the examples set forth here are not intended to be limiting or exhaustive of the possibilities.

In certain embodiments, the target blood glucose concentration level is defined to be within the upper and lower bounds of a target blood glucose concentration range for the patient. For example, one patient may strive to keep her blood glucose within the range of 70 to 200 mg/dl, while another patient may strive to keep her blood glucose within the range of 50 to 180 mg/dl. Thus, the target level defined at task 202 may fall within the desired range for the given patient. In accordance with certain embodiments, the defined target level is chosen or entered such that it represents: a lower bound of a hyperglycemic region of the patient; an upper bound of a hypoglycemic region of the patient; an ideal, nominal, or "normal" blood glucose concentration of the patient; or the like. Thus, although not always required, the target level may correspond to a patient state that might usually call for an alert, a warning, a dosage of insulin, etc.

The process 200 may continue by assigning or otherwise associating at least one threshold time period to the defined target level (task 204). Each combination of a target level and a threshold time period represents one time-to-target checkpoint. Thus, if one and only one threshold time period is associated with the defined target level, then this iteration of task 204 will result in only one time-to-target checkpoint. If, however, three different threshold time periods are associated with the defined target level, then this iteration of task 204 will result in three different time-to-target checkpoints. These concepts will be explained in more detail below with reference to FIG. 10 and FIG. 11.

The process 200 also defines and assigns certain operations of the glucose control system to be associated with each threshold time period (task 206). As used here, a system "operation" includes, without limitation, any action, function, command, operating state, condition, process, or procedure that can be achieved by, performed by, or initiated at the glucose control system. Task 206 designates particular operations that are to be triggered or preserved (as needed) when the predicted duration of time to reach the defined target level is compared against the threshold time period(s) associated with that target level.

If additional target levels are to be configured (the "No" branch of query task 208), then the process 200 returns to task 202 to define a new target level. Thereafter, one or more threshold time periods are assigned to the new target level (task 204) and the various system operations are assigned to each threshold time period of the new target level (task 206). This assignment routine can be repeated as needed to accommodate any number of different target levels, as appropriate to the particular embodiment. If no additional target levels need to be configured (the "Yes" branch of query task 208), then the process 200 saves the time-to-target checkpoints and the related configuration data for all of the defined target blood glucose levels (task 210). At this point, the glucose control system can utilize the checkpoints in an ongoing manner and process current sensor glucose readings as they become available.

Figure 10:
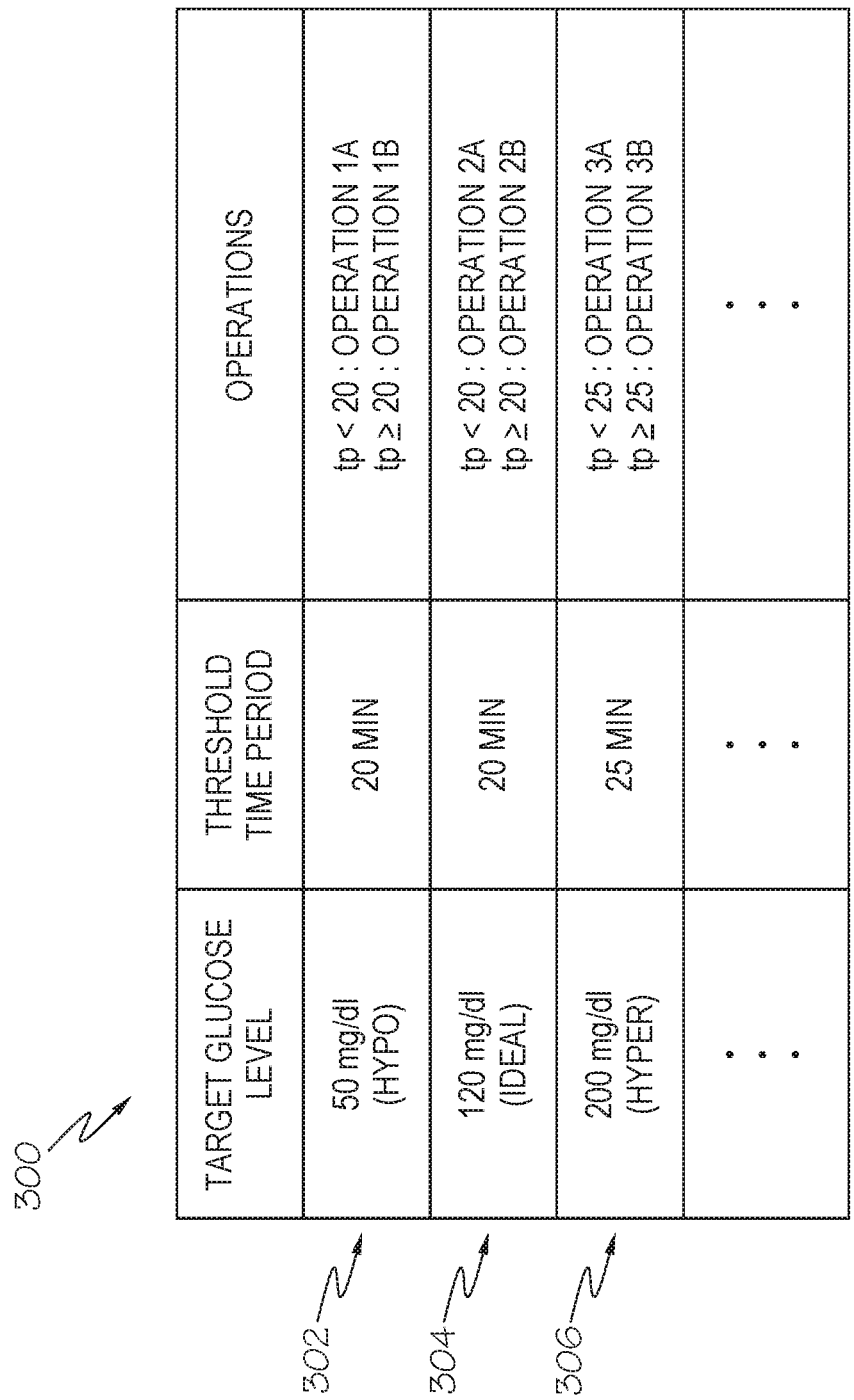
FIG. 10 is a chart that shows target blood glucose concentration levels, threshold time periods associated with the target blood glucose concentration levels, and certain operations associated with the threshold time periods.

Referring now to FIG. 10, a chart 300 shows target blood glucose concentration levels, threshold time periods associated with the target blood glucose concentration levels, and certain operations associated with the threshold time periods. FIG. 10 includes three entries corresponding to three different time-to-target checkpoints. A first time-to-target checkpoint 302 corresponds to a target blood glucose concentration level of 50 mg/dl (which may represent the upper bound of the patient's hypoglycemic region). A second time-to-target checkpoint 304 corresponds to a target blood glucose concentration level of 120 mg/dl (which may represent an ideal or desired blood glucose concentration for the patient). A third time-to-target checkpoint 306 corresponds to a target blood glucose concentration level of 200 mg/dl (which may represent the lower bound of the patient's hyperglycemic region). It should be realized that these specific values are merely exemplary in nature, and that they can vary from one patient to another if needed. These values are provided here for the sake of illustration, and are not intended to limit or otherwise restrict the scope or application of the subject matter described and claimed here in any way.

The example shown in FIG. 10 is relatively simple in that each target level has one and only one associated threshold time period. The threshold time period of 20 minutes is assigned to the target level of 50 mg/dl, the threshold time period of 20 minutes is also assigned to the target level of 120 mg/dl, and the threshold time period of 25 minutes is assigned to the target level of 200 mg/dl. Note that the first time-to-target checkpoint 302 and the second time-to-target checkpoint 304 have the same threshold time period associated therewith, namely, 20 minutes. In various embodiments, however, the different threshold time periods need not be the same, and the threshold time period corresponding to any given target level can be independently and separately chosen (relative to the other threshold time periods).

FIG. 10 also includes the different operations corresponding to each time-to-target checkpoint. FIG. 10 represents a straightforward example where two different operations are implicated by each time-to-target checkpoint. For the first time-to-target checkpoint 302, which is associated with the target blood glucose level of 50 mg/dl, a first operation (arbitrarily labeled "Operation 1A" in FIG. 10) is initiated or performed when the predicted duration of time ($t_P$) for the patient's blood glucose concentration to reach 50 mg/dl is shorter than the stated threshold time period of 20 minutes, and a second operation (arbitrarily labeled "Operation 1B" in FIG. 10) is initiated or performed when $t_P \geq 20$. A similar scheme is used for the second time-to-target checkpoint 304: Operation 2A is initiated or performed when the predicted duration of time to reach 120 mg/dl is shorter than the corresponding threshold time period of 20 minutes, and Operation 2B is initiated or performed when the predicted duration of time to reach 120 mg/dl is equal to or longer than 20 minutes. For the third time-to-target checkpoint 306, Operation 3A is initiated or performed when the predicted duration of time to reach 200 mg/dl is shorter than the corresponding threshold time period of 25 minutes, and Operation 3B is initiated or performed when the predicted duration of time to reach 200 mg/dl is equal to or longer than 25 minutes.

The operations that are controlled, initiated, and performed in connection with the time-to-target checkpoints can be designated and assigned in accordance with any desired methodology. It should be appreciated that a given operation (e.g., generate an alert, maintain the current operating state, change the insulin basal rate, etc.) could be assigned to more than one time-to-target checkpoint. Thus, even though FIG. 10 uses six different labels to identify the operations, there need not be six unique and different operations corresponding to those labels. An operation that is triggered or initiated by a time-to-target checkpoint may include one or more of the following, without limitation: altering a therapy applied to the patient (e.g., changing a rate of insulin infusion, transmitting a command signal to an insulin infusion pump, administering glucose to the patient, generating one or more insulin pump commands to control an operation of the pump, suspending insulin delivery for a given period of time, or the like); maintaining a current therapy applied to the patient by the glucose control system; temporarily deactivating a function of the glucose control system; generating an alert at the glucose control system; issuing an alarm for carbohydrate intake to prevent an impending hypoglycemic event; sending a message from the glucose control system; providing alarms, warnings, or the like; and presenting a message at the glucose control system.

It should be appreciated that this list of possible operations is not exhaustive, and that an embodiment may assign additional, different, or alternative operations to the various time-to-target checkpoints to suit the needs or preferences of the patient.

Figure 11:
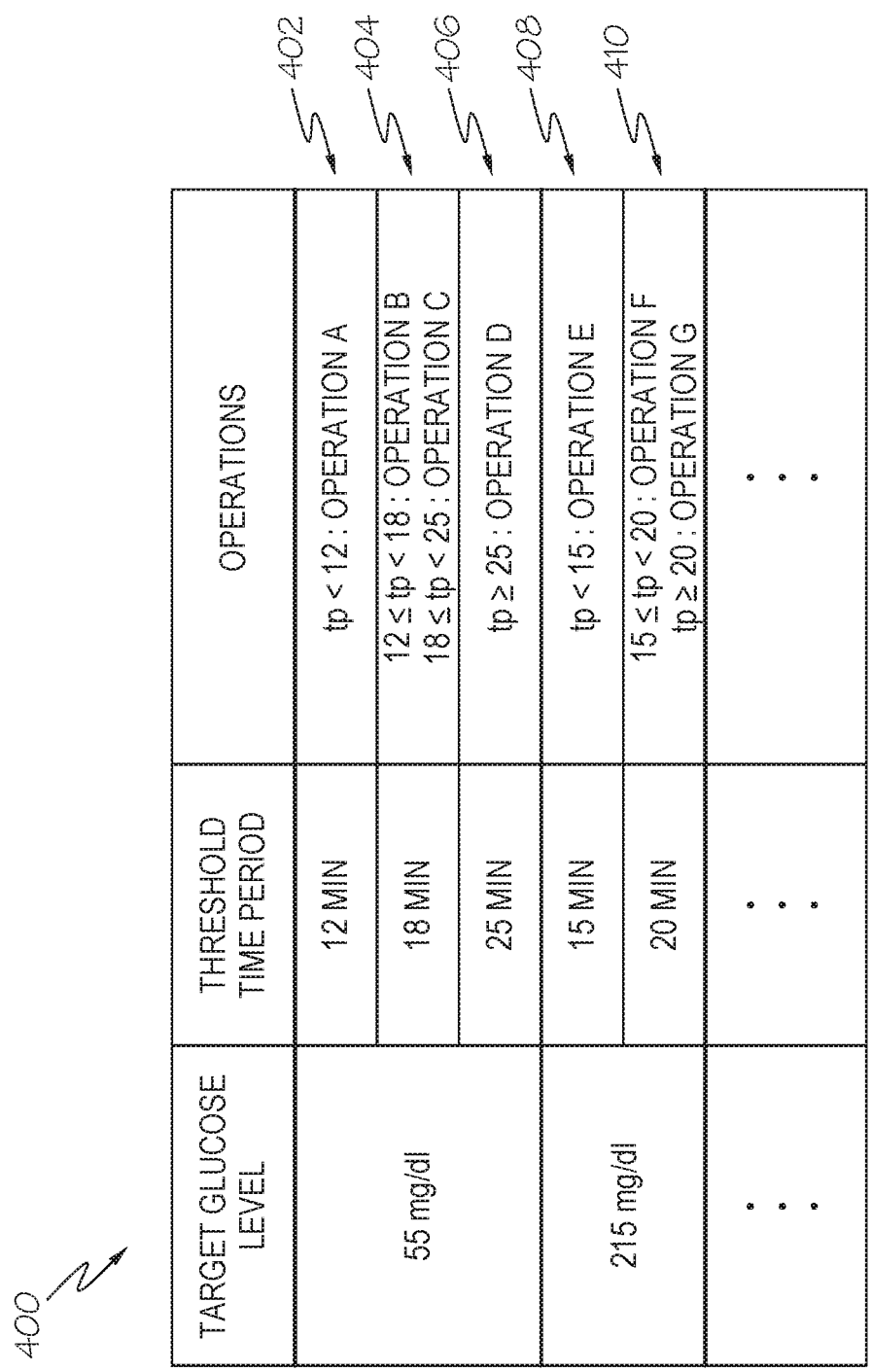
FIG. 11 is another chart that shows target blood glucose concentration levels, multiple threshold time periods associated with each target blood glucose concentration level, and certain operations associated with the threshold time periods.

FIG. 11 is another chart 400 that shows target blood glucose concentration levels, multiple threshold time periods associated with each target blood glucose concentration level, and certain operations associated with the threshold time periods. The chart 400 identifies two target blood glucose levels: 55 mg/dl and 215 mg/dl. Notably, each of these target levels includes a plurality of different threshold time periods associated therewith (in contrast, each target level in the chart 300 of FIG. 10 has one and only one threshold time period associated therewith). More specifically, the target level of 55 mg/dl has three different threshold time periods assigned to it (12 minutes, 18 minutes, and 25 minutes), and the target level of 215 mg/dl has two different threshold time periods assigned to it (15 minutes and 20 minutes). Consequently, there are three different time-to-target checkpoints for the target level of 55 mg/dl, and two different time-to-target checkpoints for the target level of 215 mg/dl. For this particular example, a first time-to-target checkpoint 402 corresponds to the 12 minute threshold time period for the target level of 55 mg/dl, a second time-to-target checkpoint 404 corresponds to the 18 minute threshold time period for the target level of 55 mg/dl, and a third time-to-target checkpoint 406 corresponds to the 25 minute threshold time period for the target level of 55 mg/dl. Moreover, a fourth time-to-target checkpoint 408 corresponds to the 15 minute threshold time period for the target level of 215 mg/dl, and a fifth time-to-target checkpoint 410 corresponds to the 20 minute threshold time period for the target level of 215 mg/dl. The specific values described here with reference to the chart 400 are merely exemplary in nature, and that they can vary from one patient to another if needed. These values are provided here for the sake of illustration, and are not intended to limit or otherwise restrict the scope or application of the subject matter described and claimed here in any way.

FIG. 11 also shows the different operations corresponding to each time-to-target checkpoint listed in the chart 400. For the first time-to-target checkpoint 402, which is associated with the target blood glucose level of 55 mg/dl, Operation A is initiated or performed when the predicted duration of time ($t_P$) for the patient's blood glucose concentration to reach 55 mg/dl is shorter than the stated threshold time period of 12 minutes. Referring to the second time-to-target checkpoint 404, which is also associated with the target level of 55 mg/dl, Operation B is initiated or performed when $12 \leq t_P < 20$, and Operation C is initiated or performed when $18 \leq t_P < 25$. For the third time-to-target checkpoint, which is also associated with the target level of 55 mg/dl, Operation D is initiated or performed when $t_P \geq 25$. Thus, the time-to-target checkpoints for the target level of 55 mg/dl define four time duration ranges that can be used to trigger the execution of different system operations: shorter than 12 minutes; between 12 and 18 minutes; between 18 and 25 minutes; and longer than 25 minutes.

A similar scheme is used for the time-to-target checkpoints that correspond to the target level of 215 mg/dl. In this regard, Operation E is initiated or performed when the predicted duration of time to reach 215 mg/dl is shorter than the corresponding threshold time period of 15 minutes. For the fifth time-to-target checkpoint 410, which is also associated with the target level of 215 mg/dl, Operation F is initiated or performed when $15 \leq t_P < 20$, and Operation G is initiated or performed when $t_P \geq 20$. Accordingly, the time-to-target checkpoints for the target level of 215 mg/dl define three time duration ranges that can be used to trigger the execution of different system operations: shorter than 15 minutes; between 15 and 20 minutes; and longer than 20 minutes.

Figure 12:
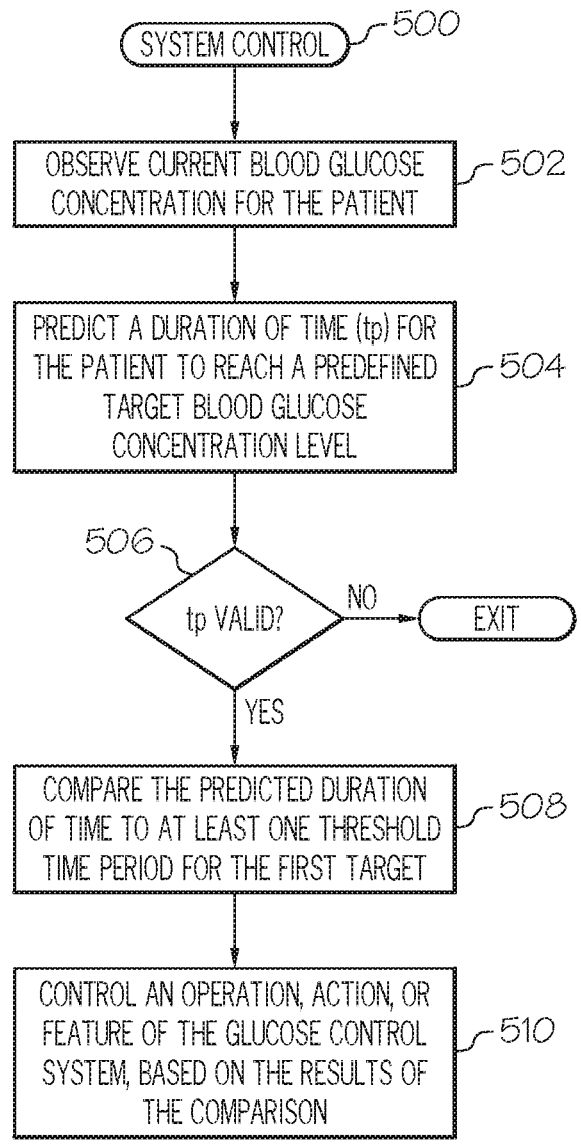
FIG. 12 is a flow chart that illustrates an exemplary embodiment of a system control process that may be performed to influence the operation of a glucose control system.

The following description assumes that a glucose control system has been configured with at least one time-to-target checkpoint and related operations that are maintained or carried out as needed. In this regard, FIG. 12 is a flow chart that illustrates an exemplary embodiment of a system control process 500 that may be performed to influence the operation of a glucose control system, such as a system of the type described above. The process observes, obtains, or calculates the current blood glucose concentration for the patient based, at least in part, on signals received from a blood-glucose sensor of the glucose control system (task 502). The current blood glucose measurement is processed to predict a duration of time, $t_P$, for the patient's blood glucose concentration to reach at least one of the predefined target blood glucose concentration levels (task 504). For ease of description, this example assumes that the process 500 considers one target level at a time. In practice, however, the process 500 may be suitably designed to concurrently or simultaneously consider a plurality of different target levels (if applicable) and to predict a plurality of different time durations. In practice, $t_P$ is based, at least in part, on the observed current blood glucose concentration. Moreover, $t_P$ may be influenced by other information, e.g., historical sensor glucose data, historical insulin pump data, usage data for the glucose control system, or the like. For example, and without limitation, $t_P$ may be calculated using any of the techniques and approaches described above.

This example assumes that task 504 actually arrives at a predicted duration of time for the given target level. An embodiment of the process 500 may check the predicted duration of time to ensure that it represents a valid or realistic value (query task 506). In this regard, the process 500 may be designed such that it only considers predicted time periods that are shorter than a predetermined threshold or limit, such as 60 minutes, 90 minutes, three hours, or the like. If the predicted duration, $t_P$, is not valid (the "No" branch of query task 506), then the process 500 may exit or return to task 502, as appropriate.

If $t_P$ is valid (the "Yes" branch of query task 506), then the process 500 continues by comparing $t_P$ to at least one threshold time period that is assigned to the target blood glucose concentration level (task 508). In other words, $t_P$ is checked against at least one of the configured time-to-target checkpoints for the patient. If the target level under consideration has only one threshold time period associated therewith (see FIG. 10 and the related description), then task 508 performs only one comparison. If, however, the target level under consideration has more than one threshold time period associated therewith (see FIG. 11 and the related description), then it may be necessary to perform more than one comparison at task 508.

The process 510 continues by controlling at least one operation, action, or feature of the glucose control system treating the patient, based on the results of the comparison(s) performed for $t_P$ (task 510). As one example where only one threshold time period is designated for the given target level, task 510 may initiate a first operation of the glucose control system when $t_P$ is shorter than specified threshold time period, and initiate a second operation of the glucose control system when $t_P$ is equal to or longer than the threshold time period, wherein the second operation is different than the first operation. Of course, if a plurality of different threshold time periods are assigned to the target level under consideration, then more than two different operations could be contemplated by the process 500. In certain embodiments, the process 500 determines which operation to control, maintain, or initiate by accessing the predefined time-to-target checkpoint configuration data.

The process 500 may be repeated as needed to consider additional target blood glucose concentration levels. For example, an iteration of the process 500 could be performed for each predefined target level for the patient such that the glucose control system can determine how best to alter the therapy administered to the patient. In certain embodiments, the process 500 is repeated as needed such that the glucose control system can identify which target level (if any) will be reached first, and take appropriate action related to that particular target level.

Figure 13:
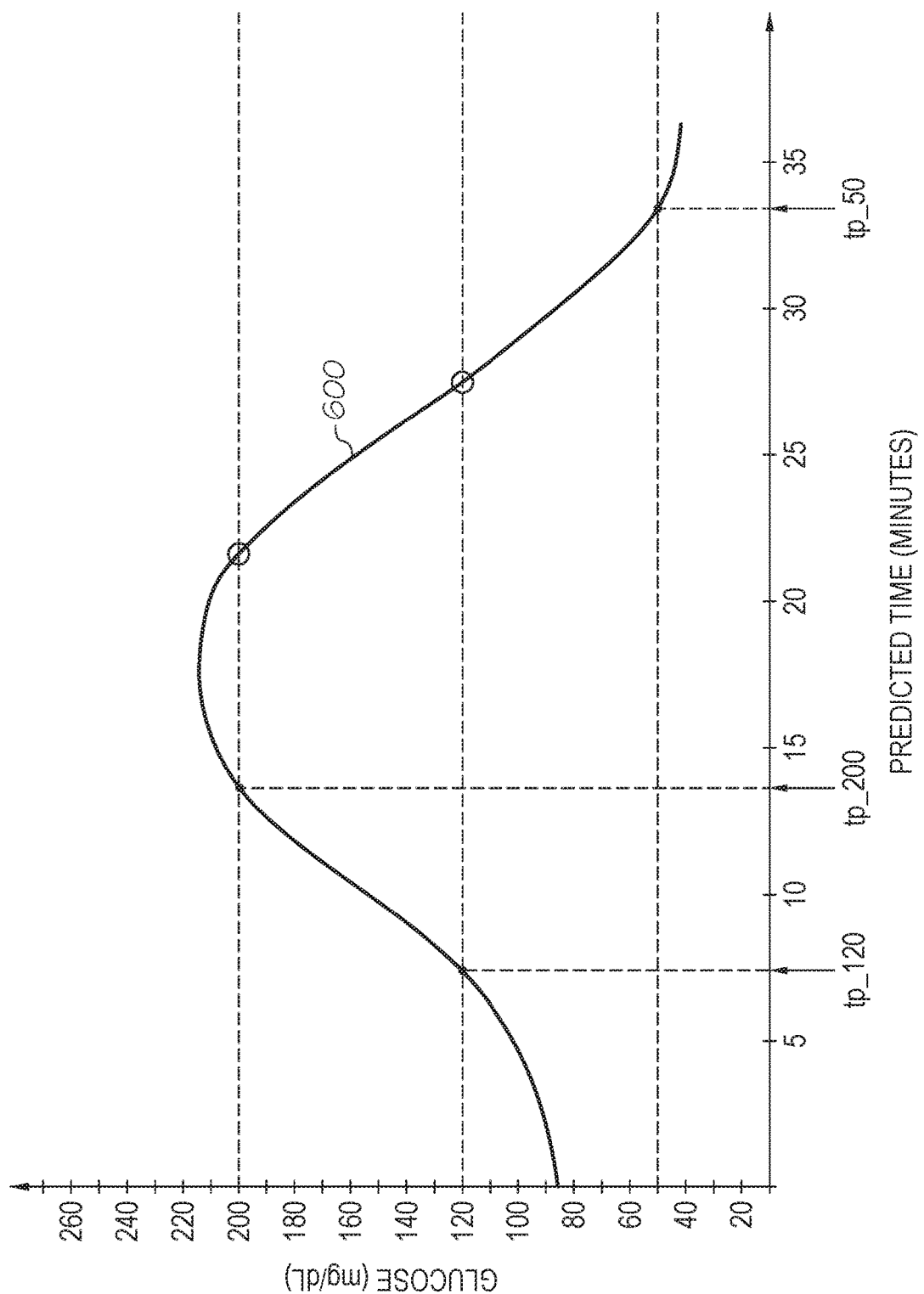
FIG. 13 is a plot of predicted glucose concentration levels over time for an exemplary patient monitoring scenario.

FIG. 13 is a plot 600 of predicted glucose concentration levels over time for an exemplary patient monitoring scenario. The plot 600 is generated at the current time, i.e., at the origin of the horizontal axis. For this example, the patient has three target levels that are monitored by the glucose control system: 50 mg/dl; 120 mg/dl; and 200 mg/dl. As depicted in FIG. 13, the plot 600 reaches the target level of 120 mg/dl after approximately seven minutes (thus, $t_{P\_120} \approx 7$ for the target level of 120 mg/dl). The plot 600 rises above 120 mg/dl, but then returns to 120 mg/dl at $t_P \approx 26$. In this scenario, the glucose control system only considers the earliest occurrence (at $t_{P\_120} \approx 7$), and disregards all other occurrences (including the occurrence at $t_P \approx 26$). Similarly, for the target level of 200 mg/dl, the system only considers the occurrence at $t_{P\_200} \approx 14$ (while disregarding the occurrence at $t_P \approx 22$). To complete this example, the predicted duration of time for the target level of 50 mg/dl is approximately 34 minutes (i.e., $t_{P\_50} \approx 34$).

Depending upon the particular embodiment, the patient treatment plan, and/or other factors, the glucose control system may alter one or more operating parameters, initiate different system operations, alter the therapy administered to the patient, or take any appropriate action at the current time, in an attempt to address the predicted excursions at $t_{P\_120} \approx 7$, at $t_{P\_200} \approx 14$, and/or at $t_{P\_50} \approx 34$. Alternatively, the glucose control system may be suitably configured to only focus on the target level of 120 mg/dl (predicted to occur at $t_{P\_120} \approx 7$), which is predicted to occur first in time. As yet another alternative approach, the glucose control system may initiate or perform certain actions that are weighted in favor of addressing conditions or issues that are predicted to occur earlier, while giving less weight (or disregarding) conditions or issues that are predicted to occur later.

Predicted time (or duration) to reach a particular glucose level has some unique advantages and uses over predicted glucose. Predicted glucose utilizes a fixed time to determine the predicted value of the glucose at a specific time in the future. It does not necessarily give information about what the glucose may be either before or after that specified time without additional calculations. Accordingly, it does not always provide a full picture, by itself, of how much time the system or the user has to respond to reaching specific glucose values.

Conversely, a predicted time approach allows the system to determine the precise time to reach one or more glucose levels in the future. This time can be used to determine if action needs to be taken now (i.e., predicted time is less than the time window set by the user, caregiver or physician), or will need to be taken relatively soon, or if no action is imminent in the near future. Typically, one or more time window thresholds are set (such as, but not limited to 5, 10, 15, 20, 25, or 30 minutes) and the predicted time (or duration of the time remaining) is compared to the threshold. If predicted time is less that the time window threshold, an alarm or action should be taken, since there is less time than was set. In some situations, if the predicted time is greater than the time window threshold, then no action should be taken at that time. If the predicted time is equal to a set time window, then logic can be used to determine if action or no action should be taken. Multiple time window thresholds may be set to give greater flexibility in responses. For instance, a large time window threshold may be used for an alert, a second shorter time window threshold can be used for an alarm, while a third still shorter time window threshold can be used to take an action, such as suspending the pump, relaying a message, changing therapy, or the like.

Generally, since predicted time only gives the predicted time to reach a specified target glucose level, the system will check one or more specific target glucose levels to be sure that upper and lower readings of glucose are considered. For instance, multiple low levels might be utilized, such as 50 mg/dl; 60 mg/dl; and 70 mg/dl (although more or less may be used and different values may be set). In this example, an alert might trigger at 70 mg/dl if the predicted time is less than the time threshold window. If the glucose level continues to fall so that the predicted time is less than the time window threshold for 60 mg/dl, then an alarm would sound. Finally, if the glucose level continues to fall so that the predicted time is less than the time window threshold for 50 mg/dl, the infusion device could be stopped, a further alarm sounded and/or a message relayed to a remote location. In addition, if more than one threshold is passed (e.g., because of a quickly dropping glucose level), multiple actions might be taken or less severe options may be bypassed in preference to more important actions. Also, the time window threshold does not need to be the same value for each level, so that they could be set to provide better sensitivity due to importance of the need to take some type of action. For instance, stopping the infusion device might have a short time window threshold, while providing an alert might have a much larger time window threshold. It should be noted that this can be applied in an analogous fashion to high glucose levels (e.g., at or above 150 mg/dl). For tight control, users may wish to also set checks around near normal glucose levels (between 80-120 mg/dl).

Predicted time provides a useful tool that allows the system to determine the time to reach specific glucose levels to be accurately known, and to then make accurate decisions on how to respond knowing the time to reach these levels. Although predicted glucose is an excellent indicator of where the individual glucose level is heading after a particular time, it does not provide specific times on when the user will pass specific time window thresholds at specific glucose values.

Unless specifically stated otherwise, as is apparent from the preceding discussion, it is to be appreciated that throughout this specification discussions utilizing terms such as "processing", "computing", "calculating", "determining", "estimating", "selecting", "identifying", "obtaining", "representing", "receiving", "transmitting", "storing", "analyzing", "associating", "measuring", "detecting", "controlling", "delaying", "initiating", "setting", "delivering", "waiting", "starting", "providing", and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device or apparatus may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be noted that although aspects of the above systems, methods, devices, processes, etc. have been described in particular orders and in particular arrangements, such specific orders and arrangements are merely examples and claimed subject matter is not limited to the orders and arrangements as described. It should also be noted that systems, devices, methods, processes, etc. described herein may be capable of being performed by one or more computing platforms. In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several non-transitory media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although what are presently considered to be example features have been illustrated and described, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. An apparatus comprising:
    an insulin infusion pump to deliver insulin to a patient;
    a glucose sensor to obtain observations of blood glucose concentration of the patient; and
    a controller to:
        assign a plurality of different threshold time periods to each of a plurality of different target blood glucose concentration levels for the patient, resulting in a plurality of different time-to-target checkpoints for the target blood glucose concentration levels, each of the plurality of different time-to-target checkpoints having a respective insulin infusion pump operation associated therewith;
        predict a respective duration of time for the patient's blood glucose concentration to reach each of the target blood glucose concentration levels using an observed current blood glucose concentration of the patient;
        identify which of the target blood glucose concentration levels is predicted to be reached first in time;
        compare the predicted duration of time for the identified target blood glucose concentration level against the threshold time periods of the plurality of different time-to-target checkpoints of the identified target blood glucose concentration level, to determine an operation of the insulin infusion pump based on the predicted duration of time and the plurality of different time-to-target checkpoints; and
        altering a therapy applied to the patient based on the determined operation of the insulin infusion pump.

2. The apparatus of claim 1, wherein:
    the controller initiates a first operation of the insulin infusion pump when the predicted duration of time is shorter than a first threshold time period; and
    the controller initiates a second operation of the insulin infusion pump when the predicted duration of time is equal to or longer than the first threshold time period.

3. The apparatus of claim 2, wherein:
    the controller initiates a third operation of the insulin infusion pump when the predicted duration of time is equal to or longer than a second threshold time period; and
    the second threshold time period is longer than the first threshold time period.

4. The apparatus of claim 1, wherein predicting the duration of time comprises:
    predicting the duration of time based, at least in part, on one or more parameters representing a sensitivity of the patient to insulin.

5. The apparatus of claim 1, wherein predicting the duration of time comprises:
    predicting the duration of time based, at least in part, on an expected change in a rate of infusion of insulin.

6. The apparatus of claim 1, wherein the determined operation comprises one or more of:
    changing a rate of insulin infusion; and
    administering glucose to the patient.

7. The apparatus of claim 1, wherein altering the therapy comprises generating one or more insulin pump commands to control the determined operation of the insulin infusion pump.

8. An insulin infusion device to deliver insulin to a patient, comprising:
    an infusion device housing; and
    a controller housed in the infusion device housing, the controller configurable to:
        assign a plurality of different threshold time periods to each of a plurality of different target blood glucose concentration levels for the patient, resulting in a plurality of different time-to-target checkpoints for the target blood glucose concentration levels, each of the plurality of different time-to-target checkpoints having a respective insulin infusion device operation associated therewith;

obtain, from a glucose sensor, observations of blood glucose concentration of the patient;

predict a respective duration of time for the patient's blood glucose concentration to reach each of the target blood glucose concentration levels using an observed current blood glucose concentration of the patient;

identify which of the target blood glucose concentration levels is predicted to be reached first in time;

compare the predicted duration of time for the identified target blood glucose concentration level against the threshold time periods of the plurality of different time-to-target checkpoints of the identified target blood glucose concentration level, to determine an operation of the insulin infusion device based on the predicted duration of time and the plurality of different time-to-target checkpoints; and altering a therapy applied to the patient based on the determined operation of the insulin infusion device.

9. The insulin infusion device of claim 8, wherein:

the controller initiates a first operation of the insulin infusion device when the predicted duration of time is shorter than a first threshold time period; and the controller initiates a second operation of the insulin infusion device when the predicted duration of time is equal to or longer than the first threshold time period.

10. The insulin infusion device of claim 9, wherein:

the controller initiates a third operation of the insulin infusion device when the predicted duration of time is equal to or longer than a second threshold time period; and the second threshold time period is longer than the first threshold time period.

11. The insulin infusion device of claim 8, wherein predicting the duration of time comprises:

predicting the duration of time based, at least in part, on one or more parameters representing a sensitivity of the patient to insulin.

12. The insulin infusion device of claim 8, wherein predicting the duration of time comprises:

predicting the duration of time based, at least in part, on an expected change in a rate of infusion of insulin.

13. The insulin infusion device of claim 8, wherein the determined operation comprises one or more of:

changing a rate of insulin infusion; and administering glucose to the patient.

* * * * *